(12) United States Patent
Kim et al.

(10) Patent No.: US 10,479,969 B2
(45) Date of Patent: *Nov. 19, 2019

(54) UTILIZATION OF WASTEWATER FOR MICROALGAL CULTIVATION

(75) Inventors: Jane Kim, San Jose, CA (US); Chung-Soon Im, Palo Alto, CA (US)

(73) Assignee: PHYCOIL BIOTECHNOLOGY INTERNATIONAL. INC., Menlo Park, CA (US)

( * ) Notice: Subject to any disclaimer, the term of this patent is extended or adjusted under 35 U.S.C. 154(b) by 565 days.

This patent is subject to a terminal disclaimer.

(21) Appl. No.: 13/270,515

(22) Filed: Oct. 11, 2011

(65) Prior Publication Data

US 2012/0088278 A1   Apr. 12, 2012

Related U.S. Application Data

(60) Provisional application No. 61/391,729, filed on Oct. 11, 2010.

(51) Int. Cl.
  *C12M 1/12* (2006.01)
  *C12M 1/00* (2006.01)

(52) U.S. Cl.
  CPC .................. *C12M 21/02* (2013.01)

(58) Field of Classification Search
  CPC ................ C12P 7/6463; C12N 1/12
  See application file for complete search history.

(56) References Cited

U.S. PATENT DOCUMENTS

| | | | |
|---|---|---|---|
| 3,142,135 | A | 7/1964 | Kathrein |
| 3,882,635 | A | 5/1975 | Yamanaka |
| 4,683,202 | A | 7/1987 | Mullis |
| 5,130,242 | A | 7/1992 | Barclay et al. |
| 6,451,567 | B1 | 9/2002 | Barclay |
| 8,278,090 | B1 | 10/2012 | Im et al. |
| 2003/0180898 | A1 | 9/2003 | Bailey et al. |
| 2006/0177920 | A1 | 8/2006 | Barclay |
| 2006/0286648 | A1 | 12/2006 | Bailey et al. |
| 2007/0082384 | A1 | 4/2007 | Barclay |
| 2007/0099280 | A1 | 5/2007 | Barclay |
| 2008/0009045 | A1 | 1/2008 | Komazawa et al. |
| 2008/0057551 | A1 | 3/2008 | Bailey et al. |
| 2008/0138851 | A1 | 6/2008 | Apt et al. |
| 2008/0199923 | A1 | 8/2008 | Barclay |
| 2009/0011480 | A1 | 1/2009 | Trimbur et al. |
| 2009/0148918 | A1 | 6/2009 | Trimbur et al. |
| 2009/0211150 | A1 | 8/2009 | Wu et al. |
| 2010/0069492 | A1 | 3/2010 | Geiringen et al. |
| 2010/0190241 | A1 | 7/2010 | Jaggi et al. |
| 2010/0239533 | A1 | 9/2010 | Apt et al. |
| 2010/0285105 | A1 | 11/2010 | Radianingtyas |
| 2011/0129884 | A1 | 6/2011 | Luy |
| 2011/0217748 | A1* | 9/2011 | Costas et al. ............. 435/173.7 |
| 2012/0171733 | A1 | 7/2012 | Im et al. |
| 2013/0102076 | A1 | 4/2013 | Licamele et al. |

FOREIGN PATENT DOCUMENTS

| | | |
|---|---|---|
| WO | WO 2007/136428 A2 | 11/2007 |
| WO | WO 2008/079724 A2 | 7/2008 |
| WO | WO 2008/145719 A1 | 12/2008 |
| WO | WO 2011/035166 A1 | 3/2011 |

OTHER PUBLICATIONS

Hu et al. Microalgal Triacylglycerols as Feedstocks for Biofuel Production: Perspectives and Advances; The Plant Journal, vol. 54 (2008) pp. 621-639.*

Burton et al. Energy From Wastewater—A Feasibility Study; Water Research Commision reposrt No. 1732/09 (2009) pp. i-114.*

Posten, C. Design Principles of Photo-Bioreactors for Cultivation of Microalgae; Engineering in Life Sciences, vol. 9, No. 3, pp. 165-177. (Year: 2009).*

Chen et al., "Growth and Phyccocyanin Formation of Spirulina Platensis in Photoheterotrophic Culture," Biotechnol. Lett., May 1996, pp. 603-608, vol. 18, No. 5.

PCT International Search Report and Written Opinion, PCT Application No. PCT/US10/49347, dated Dec. 29, 2010, 13 pages.

UTEX The Culture Collection of Algae. UTEX 2441 Apr. 1986, 1 page, [Retrieved on Dec. 13, 2010] Retrieved from the Internet<URL:http://web.biosci.utexas.edu/utex/algaeDetail.aspx?algaeID=4919>.

UTEX The Culture Collection of Algae. UTEX 2243. Jan. 12, 1999 [Retrieved on Dec. 13, 2010] Retrieved from the Internet<URL:http://web.biosci.utexas.edu/utex/search.aspx?txtSearch=2243>.

UTEX The Culture Collection of Algae, Strain Accession No. UTEX 1185 [online]. University of Texas at Austin, 1962. Retrieved from the Internet: <URL: http://web.biosci.utexas.edu/utex/algaeDetail.aspx?algaeiD=3623>, 1 page.

UTEX The Culture Collection of Algae, Strain Accession No. UTEX 2629 [online]. University of Texas at Austin, 1995. Retrieved from the Internet: <URL: URL:http://web.biosci.utexas.edu/utex/algaeDetail.aspx?algaeiD=5113>, 1 page.

U.S. Appl. No. 13/395,107, "Non-Final Office Action", dated Dec. 19, 2013, 14 pages.

U.S. Appl. No. 13/395,107, "Final Office Action", dated Aug. 5, 2014, 9 pages.

Sato, et al., "Biosynthesis of the triterpenoids, botryococcenes and tetramethylsqualene in the B race of Botryococcus braunii via the non-mevalonate pathway", Tetrahedron Letters 44, 2003, pp. 7035-7037.

(Continued)

*Primary Examiner* — Sharmila G Landau
*Assistant Examiner* — Paul C Martin
(74) *Attorney, Agent, or Firm* — Lex IP Meister, PLLC

(57) ABSTRACT

Bioreactors and methods for cultivating microalgae under heterotrophic growth conditions using fruit wastewater as a carbon source are provided herein. The heterotrophic growth conditions include low irradiance of light sufficient to initiate light-activated metabolism, but not photosynthesis. The methods provide a cost effective and environmentally friendly solution for converting wastewater from dried fruit and wine industries into products like biofuels.

16 Claims, 9 Drawing Sheets

(56) References Cited

OTHER PUBLICATIONS

Stemmer, et al., "Single-step assembly of a gene and entire plasmid from large numbers of oligodeoxyribonucleotides", Gene, vol. 164, No. 1, Oct. 16, 1995, pp. 49-53.
U.S. Appl. No. 13/395,107, "Non-Final Office Action", dated Apr. 10, 2015, 11 pages.
U.S. Appl. No. 13/395,107, Final Office Action, dated Dec. 22, 2015, 13 pages.

* cited by examiner

UTILIZATION OF WASTEWATER FOR MICROALGAL CULTIVATION

CROSS REFERENCE TO RELATED APPLICATIONS

This application claims the benefit of U.S. Provisional Application No. 61/391,729, filed Oct. 11, 2010, the entire disclosure of which is hereby incorporated by reference in its entirety for all purposes.

FIELD

The invention relates to methods, means, and systems of fermentation of microorganisms, e.g., microalgae, using wastewater derived from fruit, e.g., via washing of the fruit. The invention can be used in pharmaceutical, cosmetic and food industries, as well as for obtaining oil and biofuel from microalgae.

BACKGROUND

Most dried fruit industrial processes and wineries require water treatment facilities to treat effluents returned to the environment. Such facilities typically represent a significant investment by the business/community, and the performance of the facility (or failure thereof) can seriously impact the environment and ongoing operations, both financially and in terms of operational continuity.

Many dried fruit (e.g., raisins, prunes, dried apricots, etc.) industries use a sun-dried method and need to wash off a fine coating of dust blown onto them from sandy soil with water before packaging. When it washes away the dust on the dried fruit, some of the sugar in the dried fruit also dissolves into the water. The wash water typically contains 2-4% sugar, creating a high biological oxygen demand (BOD).

To make raisins, grapes are harvested when they reach a minimum sugar content of 19% or higher and carefully and naturally dried in the sun. Once the raisins have dried sufficiently, they are placed in large bins to store until processed. To remove rocks, dirt and sand, and organic matter, high pressure rinses with large amount of water, vacuums, wash tanks, riffles and re-rinse cycles are applied. During the washing process, a large volume of wastewater containing sugar is generated and needs to be treated before it is released to sewers.

Raisin companies in California generally produce 300 k-320 k tons of raisins every year and produce 360K-480K gal of 2-4% sugar-containing wastewater every day, year round. This is an equivalent of 40.9-54.5 tons of sugar per day and can support about 1-2 MGPY biodiesel production. Raisin wastewater contains sugar, mostly glucose, but does not generally contain much nitrogen.

In wineries, a large quantity of wastewater generation occurs during the crush process when grapes are actively being processed into juice for fermentation. This process requires large amounts of clean water for washing newly harvested grapes and results in a large wastewater output with high BOD. During the crush season, pH, BOD, total suspended solids (TSS), and nitrate levels are elevated. BOD discharge levels can approach 5,000 ppm, with values as high as 20,000 ppm in wastewater systems.

Wineries generate a strong organic wastewater that is dependent on production activities. Dissolved constituents in the wastewater include sugars, ethanol, organic acids, aldehydes, other microbial fermentation products, and soaps and detergents from clean-up operations.

Winery wastewater typically is low in pH because of organic acids produced in the fermentation process. Winery wastewater generally has sufficient phosphorus but is generally deficient in nitrogen and other trace minerals, which are necessary for efficient biological treatment.

Variability in wastewater composition depends mainly on the season and the particular operations being conducted at any given time. Certain winemaking operations—such as cleaning of the crusher, pomace conveyors, presses, and fermentation tanks—can also generate high strength wastewaters. Other process to produce wastewater includes washing of storage tanks, bottling and other equipment, and wine racking.

California produces an average of 90 percent of total U.S. wine production, and produced 631,575,325 gallon of wine in 2009. The average winery loses 7% of product post-press. For every 100 liters of juice or wine that drains from the press, only 93 liters ends up on the customer's table: the rest is lost down the drain. It can be calculated that over 44 million gallon per year of grape juice or wine is wasted as a wastewater, even though the amount of wastewater and glucose percentage varies between crushing and non-crushing seasons.

Traditional wastewater treatment systems for high BOD wastewater from the dried fruit industries and wineries are anaerobic or aerobic biological systems which let microbes consume sugar content in wastewater and lower BOD level. The most common type of biological system is an aerated lagoon or pond. Activated sludge, sequencing batch reactors (SBRs), and artificial wetlands are used by some wineries. The treated wastewater from these ponds needs to have a BOD of 40 ppm or less (depending on the location of the winery) before the winery can discharge the water to the vineyards for irrigation. The discharge level of 40 ppm as well as the restriction of standing water in an irrigation field is regionally dependent and is regulated by the Regional Water Quality Control Board (RWQCB) or the local County Department of Environmental Health. If the BOD is allowed to exceed the limits, the irrigation water can create an odor in the pond and irrigated fields, which is offensive to the wineries' customers and neighbors. If the discharge levels are significantly higher than 40 ppm BOD, the irrigation water can develop a slime layer just under the soils surface, which 'plugs' the field. This slime layer blocks the soil percolation of the water into the soil, creating standing water.

Heterotrophic fermentation of microalgae provides higher bioproductivity than photosynthetic and autotrophic growth such as open-pond system or photobioreactor system. This bioproductivity can be even higher with controlled illumination (See PCT/US2010/049347, herein incorporated by reference). In these heterotrophic conditions, organic carbon sources are needed to provide energy to microalgae. It is important to identify low cost and sustainable sugar sources for economic and sustainable production of microalgal products such as biofuels (biodiesel, renewable diesel, and biopetroleum), lipids, carotenoids, polysaccharides, biopolymers, and other chemicals.

Traditional high BOD water treatment utilizes microbes such as bacteria for biological treatment, but microalgae have not been tested and/or analyzed. The present invention demonstrates that the wastewater from dried fruit industries, e.g. raisins, fruit juice, and wineries can be used as sugar feedstock to produce valuable microalgal products.

SUMMARY

Disclosed herein is a method for utilization of wastewater from dried fruit/fruit juice industries and wineries for microalgal cultivation. It provides at least two important benefits for our society: 1. It provides a cost-effective and environmentally friendly solution for wastewater from dried fruit and wine industries; and 2. It provides a low cost sugar source which can be used for economic production of microalgal products, like biofuels (biodiesel, renewable diesel, and biopetroleum), lipids, carotenoids, polysaccharides, biopolymers, and other chemicals.

Also disclosed herein is a method for cultivating a microalgae capable of heterotrophic growth, including: incubating the microalgae under a heterotrophic growth condition for a period of time sufficient to allow the microalgae to grow, wherein the heterotrophic growth condition includes a media including a fruit wastewater carbon source, and wherein the heterotrophic growth condition further includes light.

In some aspects, the microalgae is a *Botryococcus* strain, the carbon source is raisin wastewater or wine wastewater, and the light is between 1-10 or 3-5 µmol photons $m^{-2} s^{-1}$.

In some aspects, the microalgae is a *Botryococcus sudeticus* strain. In some aspects, the microalgae is a *Botryococcus* strain. In some aspects, the microalgae is a UTEX 2629 strain. In some aspects, the microalgae is a *Botryococcus braunii* strain. In some aspects, the microalgae is a UTEX 2441 strain. In some aspects, the microalgae is a *Neochloris oleabundans* strain. In some aspects, the microalgae is a *Neochloris* strain. In some aspects, the microalgae is a UTEX 1185 strain. In some aspects, the microalgae is a *Chlamydomonas reinhardtii* strain. In some aspects, the microalgae is a *Chlamydomonas* strain. In some aspects, the microalgae is a UTEX 2243 strain. In some aspects, the microalgae comprises a photoreceptor.

In some aspects, the carbon source is raisin wastewater. In some aspects, the carbon source is wastewater from a winery.

In some aspects, the light is produced by a natural light source. In some aspects, the light is natural sun light. In some aspects, the light comprises full spectrum light or a specific wavelength of light. In some aspects, the light is produced by an artificial light source. In some aspects, the light is artificial light. In some aspects, the light is a low irradiance of light. In some aspects, the intensity of the low irradiance of light is between 0.01-1 µmol photons $m^{-2} s^{-1}$. In some aspects, the intensity of the low irradiance of light is between 1-10 µmol photons $m^{-2} s^{-1}$. In some aspects, the intensity of the low irradiance of light is between 10-100 µmol photons $m^{-2} s^{-1}$. In some aspects, the intensity of the low irradiance of light is between 100-300 µmol photons $m^{-2} s^{-1}$. In some aspects, the intensity of the low irradiance of light is between 100-300 µmol photons $m^{-2} s^{-1}$. In some aspects, the intensity of the low irradiance of light is 3-4 µmol/$m^2 s^{-1}$ photons, 2-3 µmol/$m^2 s^{-1}$ photons, 1-2 µmol/$m^2 s^{-1}$ photons, or 3-5 µmol/$m^2 s^{-1}$ photons.

In some aspects, the method further includes producing a material from the microalgae. In some aspects, the material is a polysaccharide, a pigment, a lipid, or a hydrocarbon. In some aspects, the material is a hydrocarbon.

In some aspects, the method further includes recovering the material. In some aspects, the method further includes extracting the material.

In some aspects, the method further includes processing the material. In some aspects, the processing of the material produces a processed material. In some aspects, the processed material is selected from the group consisting of a fuel, biodiesel, jet fuel, a cosmetic, a pharmaceutical agent, a surfactant, and a renewable diesel.

In some aspects, the growth rate of the microalgae in the above methods is higher than a second microalgae incubated under a second heterotrophic growth condition for a period of time sufficient to allow the microalgae to grow, wherein the second heterotrophic growth condition includes a growth media comprising a non-fruit wastewater carbon source.

Also described herein is a method of culturing microalgae, including placing a plurality of microalgae cells in the presence of a fruit wastewater-derived carbon source and a low irradiance of light.

Also described herein is a method of manufacturing a material, including: providing a microalgae capable of producing the material; culturing the microalgae in a media, wherein the media includes a fruit wastewater carbon source; applying a light to the microalgae; and allowing the microalgae to accumulate at least 10% of its dry cell weight as the material. In some aspects, the method further includes recovering the material.

Also described herein is a bioreactor system, including: a bioreactor; a culture media including a fruit wastewater carbon source, wherein the culture media is located inside the bioreactor; a microalgae adapted for heterotrophic growth, wherein the microalgae is located in the culture media; and a light source, wherein the light source is operatively coupled to the bioreactor. In some aspects, the light source produces a low irradiance of light.

In some aspects, light from the light source includes full spectrum light or a specific wavelength of light. In some aspects, light from the light source includes natural sunlight collected by a solar energy collector operatively coupled to the bioreactor, and wherein the light is transmitted to the interior of the bioreactor through an optical fiber operatively coupled to the solar collector and the bioreactor. In some aspects, light from the light source includes artificial light, wherein the artificial light is produced by a light emitted diode (LED) or a fluorescent light. In some aspects, the system further includes a power supply sufficient to power the LED or fluorescent light, wherein the power supply is operatively coupled to the bioreactor; and a light controller operatively coupled to the power supply, wherein the light controller is adapted to control the intensity and wavelength of light emitted by the LED or fluorescent light. In some aspects, the optical fibre is mounted in a transparent and protective light structure. In some aspects, the LED is mounted in a transparent and protective light structure.

Also described herein is a culture for cultivating a microalgae capable of heterotrophic growth, wherein the culture comprises the microalgae placed under a heterotrophic growth condition for a period of time sufficient to allow the microalgae to grow, wherein the heterotrophic growth condition comprises a media comprising a fruit wastewater, and wherein the heterotrophic growth condition further comprises light.

In some aspects, the microalgae is a *Botryococcus* strain, the fruit wastewater is raisin wastewater or wine wastewater, and the light is between 1-10 or 3-5 µmol photons $m^{-2} s^{-1}$.

In some aspects, the microalgae is a *Botryococcus sudeticus* strain. In some aspects, the microalgae is a *Botryococcus* strain. In some aspects, the microalgae is a UTEX 2629 strain. In some aspects, the microalgae is a *Botryococcus braunii* strain. In some aspects, the microalgae is a UTEX 2441 strain. In some aspects, the microalgae is a *Neochloris oleabundans* strain. In some aspects, the microalgae is a *Neochloris* strain. In some aspects, the microalgae is a UTEX 1185 strain. In some aspects, the microalgae is a *Chlamydomonas reinhardtii* strain. In some aspects, the microalgae is a *Chlamydomonas* strain. In some aspects, the microalgae is a UTEX 2243 strain. In some aspects, the microalgae comprises a photoreceptor.

In some aspects, the fruit wastewater is raisin wastewater. In some aspects, the fruit wastewater is wastewater from a winery.

In some aspects, the light is produced by a natural light source. In some aspects, the light is natural sun light. In some aspects, the light comprises full spectrum light or a specific wavelength of light. In some aspects, the light is produced by an artificial light source. In some aspects, the light is artificial light. In some aspects, the light is a low irradiance of light. In some aspects, the intensity of the low irradiance of light is between 0.01-1 µmol photons $m^{-2} s^{-1}$. In some aspects, the intensity of the low irradiance of light is between 1-10 µmol photons $m^{-2} s^{-1}$. In some aspects, the intensity of the low irradiance of light is between 10-100 mol photons $m^{-2} s^{-1}$. In some aspects, the intensity of the low irradiance of light is between 100-300 mol photons $m^{-2} s^{-1}$. In some aspects, the intensity of the low irradiance of light is between 100-300 mol photons $m^{-2} s^{-1}$. In some aspects, the intensity of the low irradiance of light is 3-4 µmol/$m^2s^{-1}$ photons, 2-3 µmol/$m^2s^{-1}$ photons, 1-2 µmol/$m^2s^{-1}$ photons, or 3-5 µmol/$m^2s^{-1}$ photons.

In some aspects, the culture further includes a material produced from the microalgae. In some aspects, the material is a polysaccharide, a pigment, a lipid, or a hydrocarbon. In some aspects, the material is a hydrocarbon.

BRIEF DESCRIPTION OF THE SEVERAL VIEWS OF THE DRAWINGS

These and other features, aspects, and advantages of the present invention will become better understood with regard to the following description, and accompanying drawings, where.

DETAILED DESCRIPTION

Terms used in the claims and specification are defined as set forth below unless otherwise specified.

"Axenic" means a culture of an organism that is free from contamination by other living organisms.

"Biodiesel" is a biologically produced fatty acid alkyl ester suitable for use as a fuel in a diesel engine.

The term "biomass" refers to material produced by growth and/or propagation of cells. Biomass can contain cells and/or intracellular contents as well as extracellular material. Extracellular material includes, but is not limited to, compounds secreted by a cell.

Figure 1:
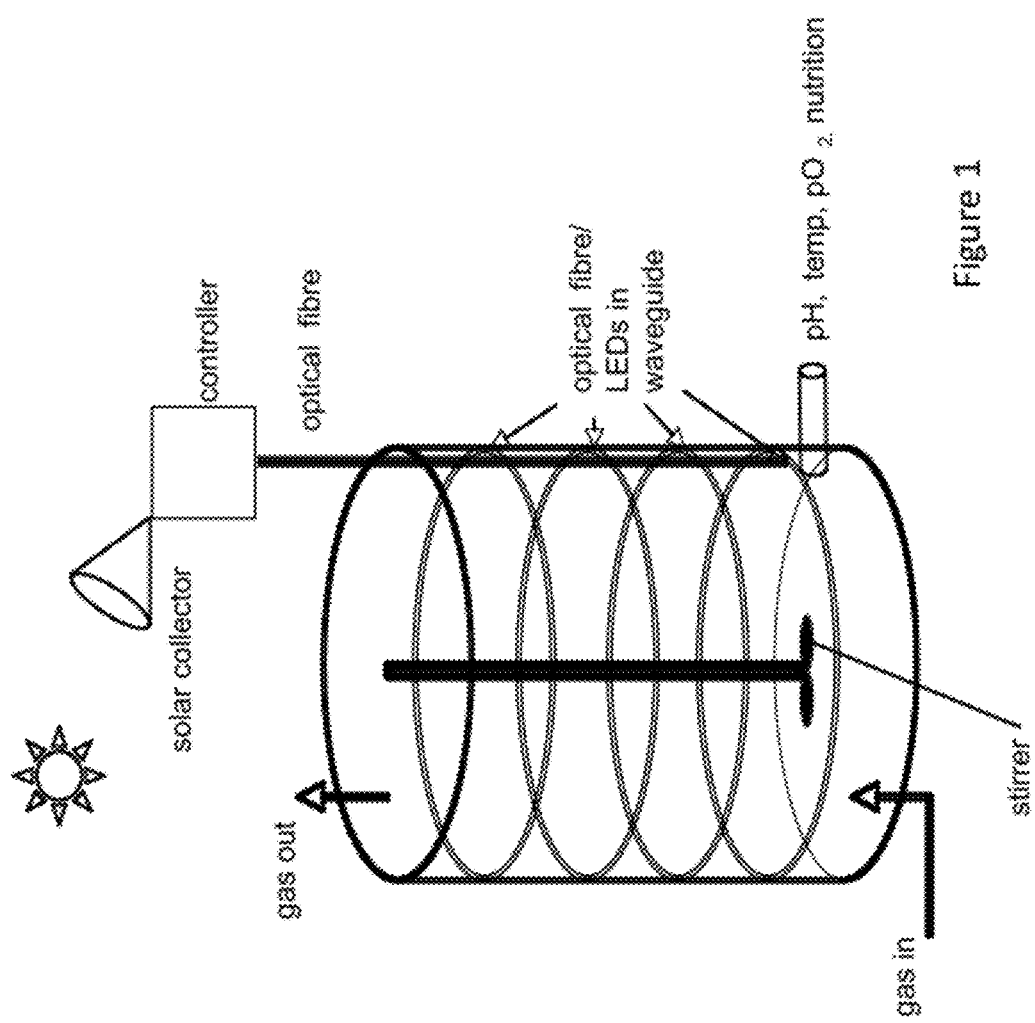
FIG. 1 is one aspect of a bioreactor.

"Bioreactor" means an enclosure or partial enclosure in which cells are cultured, optionally in suspension. FIG. 1 is an example of a bioreactor. "Photobioreactor" refers to a container, at least part of which is at least partially transparent or partially open, thereby allowing light to pass through, in which one or more microalgae cells are cultured. Photobioreactors can be closed, as in the instance of a polyethylene bag or Erlenmeyer flask, or can be open to the environment, as in the instance of an outdoor pond.

As used herein, a "catalyst" refers to an agent, such as a molecule or macromolecular complex, capable of facilitating or promoting a chemical reaction of a reactant to a product without becoming a part of the product. A catalyst thus increases the rate of a reaction, after which, the catalyst can act on another reactant to form the product. A catalyst generally lowers the overall activation energy required for the reaction such that it proceeds more quickly or at a lower temperature. Thus reaction equilibrium can be more quickly attained. Examples of catalysts include enzymes, which are biological catalysts, heat, which is a non-biological catalyst, and metal catalysts used in fossil oil refining processes.

"Cellulosic material" means the products of digestion of cellulose, including glucose and xylose, and optionally additional compounds such as disaccharides, oligosaccharides, lignin, furfurals and other compounds. Nonlimiting examples of sources of cellulosic material include sugar cane bagasses, sugar beet pulp, corn stover, wood chips, sawdust and switchgrass.

The term "co-culture", and variants thereof such as "co-cultivate", refer to the presence of two or more types of cells in the same bioreactor. The two or more types of cells can both be microorganisms, such as microalgae, or can be a microalgal cell cultured with a different cell type. The culture conditions can be those that foster growth and/or propagation of the two or more cell types or those that facilitate growth and/or proliferation of one, or a subset, of the two or more cells while maintaining cellular growth for the remainder.

The term "cofactor" is used herein to refer to any molecule, other than the substrate, that is required for an enzyme to carry out its enzymatic activity.

The term "cultivated", and variants thereof, refer to the intentional fostering of growth (increases in cell size, cellular contents, and/or cellular activity) and/or propagation (increases in cell numbers via mitosis) of one or more cells by use of intended culture conditions. The combination of both growth and propagation can be termed proliferation. The one or more cells can be those of a microorganism, such as microalgae. Examples of intended conditions include the use of a defined medium (with known characteristics such as pH, ionic strength, and carbon source), specified temperature, oxygen tension, carbon dioxide levels, and growth in a bioreactor. The term does not refer to the growth or propagation of microorganisms in nature or otherwise without direct human intervention, such as natural growth of an organism that ultimately becomes fossilized to produce geological crude oil.

As used herein, the term "cytolysis" refers to the lysis of cells in a hypotonic environment. Cytolysis is caused by excessive osmosis, or movement of water, towards the inside of a cell (hyperhydration). The cell cannot withstand the osmotic pressure of the water inside, and so it explodes.

As used herein, the terms "expression vector" or "expression construct" refer to a nucleic acid construct, generated recombinantly or synthetically, with a series of specified nucleic acid elements that permit transcription of a particular nucleic acid in a host cell. The expression vector can be part of a plasmid, virus, or nucleic acid fragment. Typically, the expression vector includes a nucleic acid to be transcribed operably linked to a promoter.

"Exogenous gene" refers to a nucleic acid transformed into a cell. A transformed cell can be referred to as a recombinant cell, into which additional exogenous gene(s) can be introduced. The exogenous gene can be from a different species (and so heterologous), or from the same species (and so homologous) relative to the cell being transformed. In the case of a homologous gene, it occupies a different location in the genome of the cell relative to the endogenous copy of the gene. The exogenous gene can be present in more than one copy in the cell. The exogenous gene can be maintained in a cell as an insertion into the genome or as an episomal molecule.

"Exogenously provided" describes a molecule provided to the culture media of a cell culture.

"Fixed carbon source" means molecule(s) containing carbon, e.g. organic, that are present at ambient temperature and pressure in solid or liquid form.

"Homogenate" means biomass that has been physically disrupted.

As used herein, "hydrocarbon" refers to: (a) a molecule containing only hydrogen and carbon atoms wherein the carbon atoms are covalently linked to form a linear, branched, cyclic, or partially cyclic backbone to which the hydrogen atoms are attached; or (b) a molecule that only primarily contains hydrogen and carbon atoms and that can be converted to contain only hydrogen and carbon atoms by one to four chemical reactions. Nonlimiting examples of the latter include hydrocarbons containing an oxygen atom between one carbon and one hydrogen atom to form an alcohol molecule, as well as aldehydes containing a single oxygen atom. Methods for the reduction of alcohols to hydrocarbons containing only carbon and hydrogen atoms are well known. Another example of a hydrocarbon is an ester, in which an organic group replaces a hydrogen atom (or more than one) in an oxygen acid. The molecular structure of hydrocarbon compounds varies from the simplest, in the form of methane ($CH_4$), which is a constituent of natural gas, to the very heavy and very complex, such as some molecules such as asphaltenes found in crude oil, petroleum, and bitumens. Hydrocarbons can be in gaseous, liquid, or solid form, or any combination of these forms, and can have one or more double or triple bonds between adjacent carbon atoms in the backbone. Accordingly, the term includes linear, branched, cyclic, or partially cyclic alkanes, alkenes, lipids, and paraffin. Examples include propane, butane, pentane, hexane, octane, triolein, and squalene.

The term "hydrogen:carbon ratio" refers to the ratio of hydrogen atoms to carbon atoms in a molecule on an atom-to-atom basis. The ratio can be used to refer to the number of carbon and hydrogen atoms in a hydrocarbon molecule. For example, the hydrocarbon with the highest ratio is methane $CH_4$ (4:1).

"Hydrophobic fraction" refers to the portion, or fraction, of a material that is more soluble in a hydrophobic phase in comparison to an aqueous phase. A hydrophobic fraction is substantially insoluble in water and usually non-polar.

As used herein, the phrase "increase lipid yield" refers to an increase in the productivity of a microbial culture by, for example, increasing dry weight of cells per liter of culture, increasing the percentage of cells that constitute lipid, or increasing the overall amount of lipid per liter of culture volume per unit time.

An "inducible promoter" is one that mediates transcription of an operably linked gene in response to a particular stimulus.

As used herein, the phrase "in operable linkage" refers to a functional linkage between two sequences, such a control sequence (typically a promoter) and the linked sequence. A promoter is in operable linkage with an exogenous gene if it can mediate transcription of the gene.

The term "in situ" means "in place" or "in its original position". For example, a culture can contain a first microalga secreting a catalyst and a second microorganism secreting a substrate, wherein the first and second cell types produce the components necessary for a particular chemical reaction to occur in situ in the co-culture without requiring further separation or processing of the materials.

A "limiting concentration of a nutrient" is a concentration in a culture that limits the propagation of a cultured organism. A "non-limiting concentration of a nutrient" is a concentration that supports maximal propagation during a given culture period. Thus, the number of cells produced during a given culture period is lower in the presence of a limiting concentration of a nutrient than when the nutrient is non-limiting. A nutrient is said to be "in excess" in a culture, when the nutrient is present at a concentration greater than that which supports maximal propagation.

As used herein, a "lipase" is a water-soluble enzyme that catalyzes the hydrolysis of ester bonds in water-insoluble, lipid substrates. Lipases catalyze the hydrolysis of lipids into glycerols and fatty acids.

"Lipids" are a class of hydrocarbon that are soluble in nonpolar solvents (such as ether and chloroform) and are relatively or completely insoluble in water. Lipid molecules have these properties because they consist largely of long hydrocarbon tails which are hydrophobic in nature. Examples of lipids include fatty acids (saturated and unsaturated); glycerides or glycerolipids (such as monoglycerides, diglycerides, triglycerides or neutral fats, and phosphoglycerides or glycerophospholipids); nonglycerides (sphingolipids, sterol lipids including cholesterol and steroid hormones, prenol lipids including terpenoids, fatty alcohols, waxes, and polyketides); and complex lipid derivatives (sugar-linked lipids, or glycolipids, and protein-linked lipids). "Fats" are a subgroup of lipids called "triacylglycerides."

The term "low irradiance of light" refers to the irradiance of light that can be applied to a microorganism while avoiding significant photoinhibition under heterotrophic conditions and the irradiance of light needed to initiate a light-activated metabolism in the microorganism. Light-activated metabolisms include, but are not limited to, a life cycle, a circadian rhythm, cell division, a biosynthetic pathway, and a transport system.

As used herein, the term "lysate" refers to a solution containing the contents of lysed cells.

As used herein, the term "lysis" refers to the breakage of the plasma membrane and optionally the cell wall of a biological organism sufficient to release at least some intracellular content, often by mechanical, viral or osmotic mechanisms that compromise its integrity.

As used herein, the term "lysing" refers to disrupting the cellular membrane and optionally the cell wall of a biological organism or cell sufficient to release at least some intracellular content.

"Microalgae" means a eukaryotic microbial organism that contains a chloroplast, and optionally that is capable of performing photosynthesis, or a prokaryotic microbial organism capable of performing photosynthesis. Microalgae include obligate photoautotrophs, which cannot metabolize a fixed carbon source as energy, as well as heterotrophs, which can live solely off of a fixed carbon source. Microalgae can refer to unicellular organisms that separate from sister cells shortly after cell division, such as *Chlamydomonas*, and can also refer to microbes such as, for example, Volvox, which is a simple multicellular photosynthetic microbe of two distinct cell types. "Microalgae" can also refer to cells such as *Chlorella* and Dunaliella. "Microalgae" also includes other microbial photosynthetic organisms that exhibit cell-cell adhesion, such as Agmenellum, Anabaena, and Pyrobotrys. "Microalgae" also includes obligate heterotrophic microorganisms that have lost the ability to perform photosynthesis, such as certain dinoflagellate algae species. Other examples of microalgae are described below.

The terms "microorganism" and "microbe" are used interchangeably herein to refer to microscopic unicellular organisms, e.g., microalgae.

As used herein, the term "osmotic shock" refers to the rupture of cells in a solution following a sudden reduction in osmotic pressure. Osmotic shock is sometimes induced to release cellular components of such cells into a solution.

"Polysaccharides" (also called "glycans") are carbohydrates made up of monosaccharides joined together by glycosidic linkages. Cellulose is an example of a polysaccharide that makes up certain plant cell walls. Cellulose can be depolymerized by enzymes to yield monosaccharides such as xylose and glucose, as well as larger disaccharides and oligosaccharides.

"Port", in the context of a bioreactor, refers to an opening in the bioreactor that allows influx or efflux of materials such as gases, liquids, and cells. Ports are usually connected to tubing leading from the bioreactor.

A "promoter" is defined as an array of nucleic acid control sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription.

As used herein, the term "recombinant" when used with reference, e.g., to a cell, or nucleic acid, protein, or vector, indicates that the cell, nucleic acid, protein or vector, has been modified by the introduction of an exogenous nucleic acid or protein or the alteration of a native nucleic acid or protein, or that the cell is derived from a cell so modified. Thus, e.g., recombinant cells express genes that are not found within the native (non-recombinant) form of the cell or express native genes that are otherwise abnormally expressed, under expressed or not expressed at all. By the term "recombinant nucleic acid" herein is meant nucleic acid, originally formed in vitro, in general, by the manipulation of nucleic acid, e.g., using polymerases and endonucleases, in a form not normally found in nature. In this manner, operably linkage of different sequences is achieved. Thus an isolated nucleic acid, in a linear form, or an expression vector formed in vitro by ligating DNA molecules that are not normally joined, are both considered recombinant for the purposes of this invention. It is understood that once a recombinant nucleic acid is made and reintroduced into a host cell or organism, it will replicate non-recombinantly, i.e., using the in vivo cellular machinery of the host cell rather than in vitro manipulations; however, such nucleic acids, once produced recombinantly, although subsequently replicated non-recombinantly, are still considered recombinant for the purposes of the invention. Similarly, a "recombinant protein" is a protein made using recombinant techniques, i.e., through the expression of a recombinant nucleic acid as depicted above.

As used herein, the term "renewable diesel" refers to alkanes (such as C:10:0, C12:0, C:14:0, C16:0 and C18:0) produced through hydrogenation and deoxygenation of lipids.

As used herein, the term "sonication" refers to a process of disrupting biological materials, such as a cell, by use of sound wave energy.

"Species of furfural" refers to 2-Furancarboxaldehyde or a derivative thereof which retains the same basic structural characteristics.

As used herein, "stover" refers to the dried stalks and leaves of a crop remaining after a grain has been harvested.

"Wastewater" is watery waste which typically contains washing water, laundry waste, feces, urine and other liquid or semi-liquid wastes. It includes some forms of municipal waste as well as secondarily treated sewage.

It must be noted that, as used in the specification and the appended claims, the singular forms "a," "an" and "the" include plural referents unless the context clearly dictates otherwise.

Microorganisms

Any species of organism that produces suitable lipid or hydrocarbon can be used, although microorganisms that naturally produce high levels of suitable lipid or hydrocarbon are preferred. Production of hydrocarbons by microorganisms is reviewed by Metzger et al. Appl Microbiol Biotechnol (2005) 66: 486-496 and A Look Back at the U.S. Department of Energy's Aquatic Species Program: Biodiesel from Algae, NREL/TP-580-24190, John Sheehan, Terri Dunahay, John Benemann and Paul Roessler (1998).

Considerations affecting the selection of microorganisms for use in the invention include, in addition to production of suitable lipids or hydrocarbons for production of oils, fuels, and oleochemicals, include: (1) high lipid content as a percentage of cell weight; (2) ease of growth; (3) ease of genetic engineering; and (4) ease of biomass processing. In particular aspects, the wild-type or genetically engineered microorganism yields cells that are at least 40%, at least 45%, at least 50%, at least 55%, at least 60%, at least 65%, or at least 70% or more lipid. Preferred organisms grow heterotrophically or can be engineered to do so using, for example, methods disclosed herein. The ease of transformation and availability of selectable markers and promoters, constitutive and/or inducible, that are functional in the microorganism affect the ease of genetic engineering. Processing considerations can include, for example, the availability of effective means for lysing the cells.

In one aspect, microorganisms include natural or engineered microorganisms that can grow under heterotrophic condition and use light as signal to control cellular processes. These can include alga such as Cyanophyta, Chlorophyta, Rhodophyta, Cryptophyta, Chlorarachniophyta, Haptophyta, Euglenophyta, Heterokontophyta, and Diatoms.

Algae

In one aspect of the present invention, the microorganism is a microalgae. Nonlimiting examples of microalgae that can be used in accordance with the present invention are described below.

More specifically, algal taxa belonging to the Cyanophyta, including Cyanophyceae, are those being Prokaryotae, which have the ability of oxygen evolution-type photosynthesis and are classified into the following orders and families. Chroococcales include Microcystaceae, Chroococcaceae, Entophysalidaceae, Chamaesiphoniaceae, Dermocarpellaceae, Xenococcaceae, and Hydrococcaceae, Oscillatoriales includes Borziaceae, Pseudanabaenaceae, Schizotrichaceae, Phormidiaceae, Oscillatoriaceae, and Homoeotrichaceae, Nostocales includes Scytonemataceae, Microchaetaceae, Rivulariaceae, and Nostocaceae, and Stigonematales includes Chlorogloeopsaceae, Capsosiraceae, Stigonemataceae, Fischerellaceae Borzinemataceae, Nostochopsaceae, and Mastigocladaceae.

Chlorophyta include Chlorophyceae, Prasinophyceae, Pedinophyceae, Trebouxiophyceae, and Ulvophyceae. More specifically, Chlorophyceae includes Acetabularia, Acicularia, Actinochloris, Amphikrikos, Anadyomene, Ankistrodesmus, Ankyra, Aphanochaete, Ascochloris, Asterococcus, Asteromonas, Astrephomene, Atractomorpha, Axilococcus, Axilosphaera, Basichlamys, Basicladia, Binuclearia, Bipedinomonas, Blastophysa, Boergesenia, Boodlea, Borodinella, Borodinellopsis, *Botryococcus*, Brachiomonas, Bracteacoccus, Bulbochaete, Caespitella, Capsosiphon, Carteria, Centrosphaera, Chaetomorpha, Chaetonema, Chaetopeltis, Chaetophora, Chalmasia, Chamaetrichon, Characiochloris, Characiosiphon, Characium, Chlamydella, Chlamydobotrys, Chlamydocapsa, *Chlamydomonas*, Chlamydopodium, Chloranomala, Chlorochydridion, Chlorochytrium, Chlorocladus, Chlorocloster, Chlorococcopsis, Chlorococcum, Chlorogonium, Chloromonas, Chlorophysalis, Chlorosarcina, Chlorosarcinopsis, Chlorosphaera, Chlorosphaeropsis, Chlorotetraedron, Chlorothecium, Chodatella, Choricystis, Cladophora, Cladophoropsis, Cloniophora, Closteriopsis, Coccobotrys, Coelastrella, Coelastropsis, Coelastrum, Coenochloris, Coleochlamys, Coronastrum, Crucigenia, Crucigeniella, Ctenocladus, Cylindrocapsa, Cylindrocapsopsis, Cylindrocystis, Cymopolia, Cystococcus, Cystomonas, Dactylococcus, Dasycladus, Deasonia, Derbesia, Desmatractum, Desmodesmus, Desmotetra, Diacanthos, Dicellula, Dicloster, Dicranochaete, Dictyochloris, Dictyococcus, Dictyosphaeria, Dictyosphaerium, Didymocystis, Didymogenes, Dilabifilum, Dimorphococcus, Diplosphaera, Draparnaldia, Dunaliella, Dysmorphococcus, Echinocoleum, Elakatothrix, Enallax, Entocladia, Entransia, Eremosphaera, Ettlia, Eudorina, Fasciculochloris, Fernandinella, Follicularia, Fottea, Franceia, Friedmannia, Fritschiella, Fusola, Geminella, Gloeococcus, Gloeocystis, Gloeodendron, Gloeomonas, Gloeotila, Golenkinia, Gongrosira, Gonium, Graesiella, Granulocystis, Gyorffiana, Haematococcus, Hazenia, Helicodictyon, Hemichloris, Heterochlamydomonas, Heteromastix, Heterotetracystis, Hormidiospora, Hormidium, Hormotila, Hormotilopsis, Hyalococcus, Hyalodiscus, Hyalogonium, Hyaloraphidium, Hydrodictyon, Hypnomonas, Ignatius, Interfilum, Kentrosphaera, Keratococcus, Kermatia, Kirchneriella, Koliella, Lagerheimia, Lautosphaeria, Leptosiropsis, Lobocystis, Lobomonas, Lola, Macrochloris, Marvania, Micractinium, Microdictyon, Microspora, Monoraphidium, Muriella, Mychonastes, Nanochlorum, Nautococcus, Neglectella, Neochloris, Neodesmus, Neomeris, Neospongiococcum, Nephrochlamys, Nephrocytium, Nephrodiella, Oedocladium, Oedogonium, Oocystella, Oocystis, Oonephris, Ourococcus, Pachycladella, Palmella, Palmellococcus, Palmellopsis, Palmodictyon, Pandorina, Paradoxia, Parietochloris, Pascherina, Paulschulzia, Pectodictyon, Pediastrum, Pedinomonas, Pedinopera, Percursaria, Phacotus, Phaeophila, Physocytium, Pilina, Planctonema, Planktosphaeria, Platydorina, Platymonas, Pleodorina, Pleurastrum, Pleurococcus, Ploeotila, Polyedriopsis, Polyphysa, Polytoma, Polytomella, Prasinocladus, Prasiococcus, Protoderma, Protosiphon, Pseudendocloniopsis, Pseudocharacium, Pseudochlorella, Pseudochlorococcum, Pseudococcomyxa, Pseudodictyosphaerium, Pseudodidymocystis, Pseudokirchneriella, Pseudopleurococcus, Pseudoschizomeris, Pseudoschroederia, Pseudostichococcus, Pseudotetracystis, Pseudotetradron, Pseudotrebouxia, Pteromonas, Pulchrasphaera, Pyramimonas, Pyrobotrys, Quadrigula, Radiofilum, Radiosphaera, Raphidocelis, Raphidonema, Raphidonemopsis, Rhizoclonium, Rhopalosolen, Saprochaete, Scenedesmus, Schizochlamys, Schizomeris, Schroederia, Schroederiella, Scotiellopsis, Siderocystopsis, Siphonocladus, Sirogonium, Sorastrum, Spermatozopsis, Sphaerella, Sphaerellocystis, Sphaerellopsis, Sphaerocystis, Sphaeroplea, Spirotaenia, Spongiochloris, Spongiococcum, Stephanoptera, Stephanosphaera, Stigeoclonium, Struvea, Tetmemorus, Tetrabaena, Tetracystis, Tetradesmus, Tetraedron, Tetrallantos, Tetraselmis, Tetraspora, Tetrastrum, Treubaria, Triploceros, Trochiscia, Trochisciopsis, Ulva, Uronema, Valonia, Valoniopsis, Ventricaria, Viridiella, Vitreochlamys, Volvox, Volvulina, Westella, Willea, Wislouchiella, Zoochlorella, Zygnemopsis, Hyalotheca, *Chlorella*, Pseudopleurococcum and Rhopalocystis. Prasinophyceae includes Heteromastix, Mammella, Mantoniella, Micromonas, Nephroselmis, Ostreococcus, Prasinocladus, Prasinococcus, Pseudoscourfielda, Pycnococcus, Pyramimonas, Scherffelia. Pedinophyceae includes Marsupiomonas, Pedinomonas, Resultor. Trebouxiophyceae includes Apatococcus, Asterochloris, Auxenochlorella, *Chlorella*, Coccomyxa, Desmococcus, Dictyochloropsis, Elliptochloris, Jaagiella, Leptosira, Lobococcus, Makinoella, Microthamnion, Myrmecia, Nannochloris, Oocystis, Prasiola, Prasiolopsis, Prototheca, Stichococcus, Tetrachlorella, Trebouxia, Trichophilus, Watanabea and Myrmecia. Ulvophyceae includes Acrochaete, Bryopsis, Cephaleuros, Chlorocystis, Enteromorpha, Gloeotilopsis, Halochlorococcum, Ostreobium, Pirula, Pithophora, Planophila, Pseudendoclonium, Trentepohlia, Trichosarcina, Ulothrix, Bolbocoleon, Chaetosiphon, Eugomontia, Oltmannsiellopsis, Pringsheimiella, Pseudodendroclonium, Pseudulvella, Sporocladopsis, Urospora, and Wittrockiella.

Rhodophyta include Acrochaetium, Agardhiella, Antithamnion, Antithamnionella, Asterocytis, Audouinella, Balbiania, Bangia, Batrachospermum, Bonnemaisonia, Bostrychia, Callithamnion, Caloglossa, Ceramium, Champia, Chroodactylon, Chroothece, Compsopogon, Compsopogonopsis, Cumagloia, Cyanidium, Cystoclonium, Dasya, Digenia, Dixoniella, Erythrocladia, Erythrolobas, Erythrotrichia, Flintiella, Galdieria, Gelidium, Glaucosphaera, Goniotrichum, Gracilaria, Grateloupia, Griffithsia, Hildenbrandia, Hymenocladiopsis, Hypnea, Laingia, Membranoptera, Myriogramme, Nemalion, Nemnalionopsis, Neoagardhiella, Palmaria, Phyllophora, Polyneura, Polysiphonia, Porphyra, Porphyridium, Pseudochantransia, Pterocladia, Pugetia, Rhodella, Rhodochaete, Rhodochorton, Rhodosorus, Rhodospora, Rhodymenia, Seirospora, Selenastrum, Sirodotia, Solieria, Spermothamnion, Spyridia, Stylonema, Thorea, Trailiella and Tuomeya.

Cryptophyta include Cryptophycease. More specifically, Campylomonas, Chilomonas, Chroomonas, Cryptochrysis, Cryptomonas, Goniomonas, Guillardia, Hanusia, Hemiselmis, Plagioselmis, Proteomonas, Pyrenomonas, Rhodomonas and Stroreatula.

Chlorarachniophyta include Chlorarachnion, Lotharella and Chattonella.

Haptophyta include Apistonema, Chrysochromulina, Coccolithophora, Corcontochrysis, Cricosphaera, Diacronema, Emiliana, Pavlova, Ruttnera, Cruciplacolithus, Prymnesium, Isochrysis, Calyptrosphaera, Chrysotila, Coccolithus, Dicrateria, Heterosigma, Hymenomonas, Imantonia, Gephyrocapsa, Ochrosphaera, Phaeocystis, Platychrysis, Pseudoisochrysis, Syracosphaera and Pleurochrysis.

Euglenophyta include stasia, Colacium, Cyclidiopsis, Distigma, Euglena, Eutreptia, Eutreptiella, Gyropaigne, Hyalophacus, Khawkinea Astasia, Lepocinclis, Menoidium, Parmidium, Phacus, Rhabdomonas, Rhabdospira, Tetruetreptia and Trachelomonas Heterokontophyta include Bacillariophyceae, Phaeophyceae, Pelagophyceae, Xanthophyceae, Eustigmatophyceae, Syanurophyceae, Phaeothamniophyceae and Raphidophyceae. More specifically, Bacillariophyceae includes Achnanthes, Amphora, Chaetoceros, Bacillaria, Nitzschia, Navicula, and Pinnularia. Phaeophyceae includes Ascoseira, Asterocladon, Bodanella, Desmarestia, Dictyocha, Dictyota, Ectocarpus, Halopteris, Heribaudiella, Pleurocladia, Porterinema, Pylaiella, Sorocarpus, Spermatochnus, Sphacelaria and Waerniella. Pelagophyceae includes Aureococcus, Aureoumbra, Pelagococcus, Pelagomonas, Pulvinaria and Sarcinochrysis. Xanthophyceae includes Chloramoebales, Rhizochloridales, Mischococcales, Tribonematales, and Vaucheriales. Eustigmatophyceae includes Chloridella, Ellipsoidion, Eustigmatos, Monodopsis, Monodus, Nannochloropsis, Polyedriella, Pseudocharaciopsis, Pseudostaurastrum and Vischeria Syanurophyceae includes allomonas, Synura and Tessellaria. Phaeothamniophyceae includes haeobotrys and Phaeothamnion. Raphidophyceae includes Olisthodiscus, Vacuolaria and Fibrocapsa.

Diatoms include Bolidophyceae, Coscinodiscophyceae, Dinophyceae and Alveolates. Bolidophyceae include Bolidomonas, Chrysophyceae, Giraudyopsis, Glossomastix, Chromophyton, Chrysamoeba, Chrysochaete, Chrysodidymus, Chrysolepidomonas, Chrysosaccus, Chrysosphaera, Chrysoxys, Cyclonexis, Dinobryon, Epichrysis, Epipyxis, Hibberdia, Lagynion, Lepochromulina, Monas, Monochrysis, Paraphysomonas, Phaeoplaca, Phaeoschizochlamys, Picophagus, Pleurochrysis, Stichogloea and Uroglena. Coscinodiscophyceae include Bacteriastrum, Bellerochea, Biddulphia, Brockmanniella, Corethron, Coscinodiscus, Eucampia, Extubocellulus, Guinardia, Helicotheca, Leptocylindrus, Leyanella, Lithodesmium, Melosira, Minidiscus, Odontella, Planktoniella, Porosira, Proboscia, Rhizosolenia, Stellarima, Thalassionema, Bicosoecid, Symbiomonas, Actinocyclus, Amphora, Arcocellulus, Detonula, Diatoma, Ditylum, Fragilariophyceae, Asterionellopsis, Delphineis, Grammatophora, Nanofrustulum, Synedra and Tabularia. Dinophyceae includes Adenoides, Alexandrium, Amphidinium, Ceratium, Ceratocorys, Coolia, Crypthecodinium, Exuviaella, Gambierdiscus, Gonyaulax, Gymnodinium, Gyrodinium, Heterocapsa, Katodinium, Lingulodinium, Pfiesteria, Polarella, Protoceratium, Pyrocystis, Scrippsiella, Symbiodinium, Thecadinium, Thoracosphaera, and Zooxanthella. Alveolates include Cystodinium, Glenodinium, Oxyrrhis, Peridinium, Prorocentrum, and Woloszynskia.

Methods of Culturing Microorganisms and Bioreactors

Microorganisms are generally cultured both for purposes of conducting genetic manipulations and for subsequent production of hydrocarbons (e.g., lipids, fatty acids, aldehydes, alcohols, and alkanes). The former type of culture is generally conducted on a small scale and initially, at least, under conditions in which the starting microorganism can grow. Culture for purposes of hydrocarbon production is usually conducted on a large scale. Preferably a fixed carbon source (e.g. a feedstock) is present. The culture can also be exposed to light some or all of the time.

Bioreactor

Microalgae can be cultured in liquid media. The culture can be contained within a bioreactor. Microalgae can also be cultured in photobioreactors that contain a fixed carbon source and allow light to strike the cells. Exposure of microalgae cells to light, even in the presence of a fixed carbon source that the cells transport and utilize, can accelerate growth compared to culturing cells in the dark. Culture condition parameters can be manipulated to optimize total hydrocarbon production, the combination of hydrocarbon species produced, and/or production of a hydrocarbon species.

FIG. 1 is one aspect of a bioreactor of the invention. In one aspect a bioreactor is a photobioreactor. In one aspect, a bioreactor system can be used for cultivating microalgae. The bioreactor system can include a container and an irradiation assembly, where the irradiation assembly is operatively coupled to the container.

In one aspect, a bioreactor is a fermentation tank used for industrial fermentation processes.

In some aspects, a bioreactor includes glass, metal or plastic tanks, equipped with, e.g., gauges and settings to control aeration, stir rate, temperature, pH, and other parameters of interest. Generally the gauges and settings are operatively coupled to the bioreactor.

In one aspect, a bioreactor can be small enough for bench-top applications (5-10 L or less) or up to 120,000 L or larger in capacity for large-scale industrial applications.

In some aspects, the bioreactor system can include a light-diffusing structure or a plurality of light-diffusing structures. In some aspects, one or more of the light-diffusing structures from the plurality of light-diffusing structures are located along the interior surface of the bioreactor. In some aspects, the light-diffusing structure is operatively coupled to the bioreactor.

The bioreactor system can include one or more optical fibers and/or a plurality of light sources and/or a light source. In some aspects, the one or more optical fibres are mounted in protective and optically transparent lighting structures. In some aspects, the optical fiber is operatively coupled to the bioreactor. In some aspects, the light source is operatively coupled to the bioreactor.

In some aspects, the bioreactor system can include a lighting structure operatively coupled to a bioreactor. In certain aspects herein a lighting structure can have any shape or form as it directs light signal to the interior of a bioreactor. The bioreactor system can also include at least one optical fiber extending from a first end of at least one of the one or more optical fibers to a portion of a solar energy collector. In some aspects, the solar energy collector is operatively coupled to the bioreactor. The optical fiber can be adapted to optically couple the solar energy collector to the bioreactor. The optical fiber can be optically coupled (directly or indirectly) to the solar energy collector.

In some aspects, the bioreactor system includes a plurality of light sources operatively coupled to the bioreactor. The plurality of light sources can include multiple LEDs. The plurality of light sources comprising multiple LEDs can be operable to supply full spectrum or a specific wavelength of artificial light to a bioreactor.

In one aspect, an LED is mounted in protective and optically transparent lighting structures. In one aspect the LED is an array of LEDs.

In some aspects, microalgae can be grown and maintained in closed bioreactors made of different types of transparent or semitransparent material. Such material can include Plexiglass™ enclosures, glass enclosures, bags made from substances such as polyethylene, transparent or semitransparent pipes, and other materials. Microalgae can be grown and maintained in open bioreactors such as raceway ponds, settling ponds, and other non-enclosed containers.

The gas content of a bioreactor to grow microorganisms like microalgae can be manipulated. Part of the volume of a bioreactor can contain gas rather than liquid. Gas inlets can be used to pump gases into the bioreactor. Any gas can be pumped into a bioreactor, including air, air/$O_2$ mixtures, noble gases such as argon and others. The rate of entry of gas into a bioreactor can also be manipulated. Increasing gas flow into a bioreactor increases the turbidity of a culture of microalgae. Placement of ports conveying gases into a bioreactor can also affect the turbidity of a culture at a given gas flow rate. Air/$O_2$ mixtures can be modulated to generate optimal amounts of $O_2$ for maximal growth by a particular organism. Microalgae grow significantly faster in the light under, for example, 3% $O_2$/97% air than in 100% air. 3% $O_2$/97% air is approximately 100-fold more $O_2$ than found in air. For example, air:$O_2$ mixtures of about 99.75% air:0.25% $O_2$, about 99.5% air:0.5% $O_2$, about 99.0% air:1.00% $O_2$, about 98.0% air:2.0% $O_2$, about 97.0% air:3.0% $O_2$, about 96.0% air:4.0% $O_2$, and about 95.00% air:5.0% $O_2$ can be infused into a bioreactor or bioreactor.

Microalgae cultures can also be subjected to mixing using devices such as spinning blades and impellers, rocking of a culture, stir bars, infusion of pressurized gas, and other instruments.

Bioreactors can have ports allowing entry of gases, solids, semisolids and liquids into the chamber containing the microalgae. Ports are usually attached to tubing or other means of conveying substances. Gas ports, for example, convey gases into the culture. Pumping gases into a bioreactor can serve to both feed cells $O_2$ and other gases and to aerate the culture and therefore generate turbidity. The amount of turbidity of a culture varies as the number and position of gas ports is altered. For example, gas ports can be placed along the bottom of a cylindrical polyethylene bag. Microalgae grow faster when $O_2$ is added to air and bubbled into a bioreactor.

Bioreactors preferably have one or more ports that allow media entry. It is not necessary that only one substance enter or leave a port. For example, a port can be used to flow culture media into the bioreactor and then later can be used for sampling, gas entry, gas exit, or other purposes. In some instances a bioreactor is filled with culture media at the beginning of a culture and no more growth media is infused after the culture is inoculated. In other words, the microalgal biomass is cultured in an aqueous medium for a period of time during which the microalgae reproduce and increase in number; however quantities of aqueous culture medium are not flowed through the bioreactor throughout the time period. Thus in some aspects, aqueous culture medium is not flowed through the bioreactor after inoculation.

In other instances culture media can be flowed though the bioreactor throughout the time period during which the microalgae reproduce and increase in number. In some aspects media is infused into the bioreactor after inoculation but before the cells reach a desired density. In other words, a turbulent flow regime of gas entry and media entry is not maintained for reproduction of microalgae until a desired increase in number of said microalgae has been achieved.

Bioreactors preferably have one or more ports that allow gas entry. Gas can serve to both provide nutrients such as $O_2$ as well as to provide turbulence in the culture media. Turbulence can be achieved by placing a gas entry port below the level of the aqueous culture media so that gas entering the bioreactor bubbles to the surface of the culture. One or more gas exit ports allow gas to escape, thereby preventing pressure buildup in the bioreactor. Preferably a gas exit port leads to a "one-way" valve that prevents contaminating microorganisms from entering the bioreactor. In some instances cells are cultured in a bioreactor for a period of time during which the microalgae reproduce and increase in number, however a turbulent flow regime with turbulent eddies predominantly throughout the culture media caused by gas entry is not maintained for all of the period of time. In other instances a turbulent flow regime with turbulent eddies predominantly throughout the culture media caused by gas entry can be maintained for all of the period of time during which the microalgae reproduce and increase in number. In some instances a predetermined range of ratios between the scale of the bioreactor and the scale of eddies is not maintained for the period of time during which the microalgae reproduce and increase in number. In other instances such a range can be maintained.

Bioreactors preferably have at least one port that can be used for sampling the culture. Preferably a sampling port can be used repeatedly without altering compromising the axenic nature of the culture. A sampling port can be configured with a valve or other device that allows the flow of sample to be stopped and started. Alternatively a sampling port can allow continuous sampling. Bioreactors preferably have at least one port that allows inoculation of a culture. Such a port can also be used for other purposes such as media or gas entry.

In one aspect, a bioreactor with an irradiation system can be used to produce hydrocarbon from *Botryococcus*. Botryococcenes are unbranched isoprenoid triterpenes having the formula $C_nH_{2n-10}$. The A race produces alkadienes and alkatrienes (derivatives of fatty acids) wherein n is an odd number 23 through 31. The B race produces botryococcenes wherein n is in the range 30 through 40. These can be biofuels of choice for hydrocracking to gasoline-type hydrocarbons.

Media

Microalgal culture media typically contains components such as a fixed nitrogen source, trace elements, optionally a buffer for pH maintenance, and phosphate. Other components can include a fixed carbon source such as acetate or glucose, and salts such as sodium chloride, particularly for seawater microalgae. Examples of trace elements include zinc, boron, cobalt, copper, manganese, and molybdenum in, for example, the respective forms of $ZnCl_2$, $H_3BO_3$, $CoCl_2.6H_2O$, $CuCl_2.2H_2O$, $MnCl_2.4H_2O$ and $(NH_4)_6Mo_7O_24.4H_2O$.

For organisms able to grow on a fixed carbon source, the fixed carbon source can be, for example, glucose, fructose, sucrose, galactose, xylose, mannose, rhamnose, N-acetylglucosamine, glycerol, floridoside, and/or glucuronic acid. The one or more carbon source(s) can be supplied at a concentration of less than 50 µM, at least about 50 µM, at least about 100 µM, at least about 500 µM, at least about 5 mM, at least about 50 mM, at least about 500 mM, and more than 500 mM of one or more exogenously provided fixed carbon source(s). The one or more carbon source(s) can be supplied at a less than 1%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% of the media. The one or more carbon source(s) can also be supplied at a percentage of the media between the above noted percentages, e.g., 2.5% or 3.7% of the media.

In some aspects, the invention provides a method for the cultivation of microalgae using wastewater from the dried fruit, fruit juice, and winery industries.

In an aspect, the pH of wastewater is adjusted to a desired level using an acid or a base. In another aspect, the pH of wastewater is adjusted by using other wastewater with a different pH. In one example, the pH of raisin wastewater (low pH) is adjusted using wastewater from the peach cannery industries (high pH).

In one aspect, the wastewater is sterilized using a filtration system. In another aspect, the wastewater can be sterilized by a continuous sterilization system or other methods such as, e.g., heating, irradiation, and ozone.

In some aspects, the wastewater is supplemented with a nitrogen source such as nitrate, nitrite, ammonium, urea, casein hydrolysate, yeast extract, beef extract, peptones, and nitrogen-rich wastewater such as from a livestock farm.

In some aspects, the wastewater is supplemented with other nutrients including, but not limited to, phosphate, magnesium, sulfate, calcium, sodium, manganese, zinc, cobalt, molybdenum, borate, citrate, iron, copper, selenium, silicon, and vitamins.

In some aspects, wastewater is used as a sole carbon source. In another aspect, the wastewater is mixed with regular microalgal culture media in different portions. In some aspects, the portion of wastewater can be 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% of the media. The one or more wastewater carbon source(s) can also be supplied at a percentage of the media between the above noted percentages, e.g., 2.5% or 3.7% of the media.

In some aspects, the wastewater is used to feed a traditional submerged liquid fermentor. In another aspect, the wastewater is used to feed a solid-state fermentation device.

In some aspects, the wastewater is used to grow microalgae and cyanobacteria in combination with or without controlled illumination.

Some microorganisms naturally grow on or can be engineered to grow on a fixed carbon source that is a heterogeneous source of compounds such as municipal waste, secondarily treated sewage, wastewater, and other sources of fixed carbon and other nutrients such as sulfates, phosphates, and nitrates. The sewage component serves as a nutrient source in the production of hydrocarbons, and the culture provides an inexpensive source of hydrocarbons.

Other culture parameters can also be manipulated, such as the pH of the culture media, the identity and concentration of trace elements and other media constituents.

Microorganisms useful in accordance with the methods of the present invention are found in various locations and environments throughout the world. As a consequence of their isolation from other species and their resulting evolutionary divergence, the particular growth medium for optimal growth and generation of lipid and/or hydrocarbon constituents can vary. In some cases, certain strains of microorganisms can be unable to grow on a particular growth medium because of the presence of some inhibitory component or the absence of some essential nutritional requirement required by the particular strain of microorganism.

Solid and liquid growth media are generally available from a wide variety of sources, and instructions for the preparation of particular media that is suitable for a wide variety of strains of microorganisms can be found, for example, online at a site maintained by the University of Texas at Austin for its culture collection of algae (UTEX).

Process conditions can be adjusted to increase the yield of lipids suitable for a particular use and/or to reduce production cost. For example, in certain aspects, a microbe (e.g., microalgae) is cultured in the presence of a limiting concentration of one or more nutrients, such as, for example, carbon and/or nitrogen, phosphorous, or sulfur, while providing an excess of fixed carbon energy such as glucose. Nitrogen limitation tends to increase microbial lipid yield over microbial lipid yield in a culture in which nitrogen is provided in excess. In particular aspects, the increase in lipid yield is at least about: 10%, 20%, 30%, 40%, 50%, 75%, 100%, 200%, 300%, 400%, or 500%. The microbe can be cultured in the presence of a limiting amount of a nutrient for a portion of the total culture period or for the entire period. In particular aspects, the nutrient concentration is cycled between a limiting concentration and a non-limiting concentration at least twice during the total culture period.

Heterotrophic Growth and Light

Microorganisms can be cultured under heterotrophic growth conditions in which a fixed carbon source provides energy for growth and lipid accumulation.

Standard methods for the heterotrophic growth and propagation of microalgae are known (see for example Miao and Wu, J Biotechnology, 2004, 11:85-93 and Miao and Wu, Biosource Technology (2006) 97:841-846).

For hydrocarbon production, cells, including recombinant cells of the invention described herein, can be cultured or fermented in large quantities. The culturing can be in large liquid volumes, such as in suspension cultures as an example. Other examples include starting with a small culture of cells which expand into a large biomass in combination with cell growth and propagation as well as hydrocarbon production. Bioreactors or steel fermentors can be used to accommodate large culture volumes. A bioreactor can include a fermentor. A fermentor similar those used in the production of beer and/or wine can be suitable, as are extremely large fermentors used in the production of ethanol.

Appropriate nutrient sources for culture in a fermentor are provided. These include raw materials such as one or more of the following: a fixed carbon source such as glucose, corn starch, depolymerized cellulosic material, sucrose, sugar cane, sugar beet, lactose, milk whey, or molasses; a fat source, such as fats or vegetable oils; a nitrogen source, such as protein, soybean meal, cornsteep liquor, ammonia (pure or in salt form), nitrate or nitrate salt, or molecular nitrogen; and a phosphorus source, such as phosphate salts. Additionally, a fermentor allows for the control of culture conditions such as temperature, pH, oxygen tension, and carbon dioxide levels. Optionally, gaseous components, like oxygen or nitrogen, can be bubbled through a liquid culture. Other Starch (glucose) sources such as wheat, potato, rice, and sorghum. Other carbon sources include process streams such as technical grade glycerol, black liquor, organic acids such as acetate, and molasses. Carbon sources can also be provided as a mixture, such as a mixture of sucrose and depolymerized sugar beet pulp.

A fermentor can be used to allow cells to undergo the various phases of their growth cycle. As an example, an inoculum of hydrocarbon-producing cells can be introduced into a medium followed by a lag period (lag phase) before the cells begin growth. Following the lag period, the growth rate increases steadily and enters the log, or exponential, phase. The exponential phase is in turn followed by a slowing of growth due to decreases in nutrients and/or increases in toxic substances. After this slowing, growth stops, and the cells enter a stationary phase or steady state, depending on the particular environment provided to the cells.

Hydrocarbon production by cells disclosed herein can occur during the log phase or thereafter, including the stationary phase wherein nutrients are supplied, or still available, to allow the continuation of hydrocarbon production in the absence of cell division.

Preferably, microorganisms grown using conditions described herein and known in the art comprise at least about 20% by weight of lipid, preferably at least about 40% by weight, more preferably at least about 50% by weight, and most preferably at least about 60% by weight.

In an alternate heterotrophic growth method in accordance with the present invention, microorganisms can be cultured using depolymerized cellulosic biomass as a feedstock. Cellulosic biomass (e.g., stover, such as corn stover) is inexpensive and readily available; however, attempts to use this material as a feedstock for yeast have failed. In particular, such feedstock has been found to be inhibitory to yeast growth, and yeast cannot use the 5-carbon sugars produced from cellulosic materials (e.g., xylose from hemicellulose). By contrast, microalgae can grow on processed cellulosic material. Accordingly, the invention provides a method of culturing microalgae in the presence of a cellulosic material and/or a 5-carbon sugar.

Suitable cellulosic materials include residues from herbaceous and woody energy crops, as well as agricultural crops, i.e., the plant parts, primarily stalks and leaves, not removed from the fields with the primary food or fiber product. Examples include agricultural wastes such as sugarcane bagasse, rice hulls, corn fiber (including stalks, leaves, husks, and cobs), wheat straw, rice straw, sugar beet pulp, citrus pulp, citrus peels; forestry wastes such as hardwood and softwood thinnings, and hardwood and softwood residues from timber operations; wood wastes such as saw mill wastes (wood chips, sawdust) and pulp mill waste; urban wastes such as paper fractions of municipal solid waste, urban wood waste and urban green waste such as municipal grass clippings; and wood construction waste. Additional cellulosics include dedicated cellulosic crops such as switchgrass, hybrid poplar wood, and miscanthus, fiber cane, and fiber sorghum. Five-carbon sugars that are produced from such materials include xylose.

In still another alternative heterotrophic growth method in accordance with the present invention, which itself can optionally be used in combination with the methods described above, sucrose, produced by example from sugar cane or sugar beet, is used as a feedstock.

Heterotrophic growth can include the use of both light and fixed carbon source(s) for cells to grow and produce hydrocarbons. Heterotrophic growth can be conducted in a photobioreactor.

Bioreactors can be exposed to one or more light sources to provide microalgae with a light signal. A light signal can be provided via light directed to a surface of the bioreactor by a light source. Preferably the light source provides an intensity that is sufficient for the cells to grow, but not so intense as to cause oxidative damage or cause a photoinhibitive response. In some instances a light source has a wavelength range that mimics or approximately mimics the range of the sun. In other instances a different wavelength range is used. Bioreactors can be placed outdoors or in a greenhouse or other facility that allows sunlight to strike the surface. In some aspects, photon intensities for species of the genus *Botryococcus* are between 25 and 500 $\mu$mE m$^{-2}$ s$^{-1}$ (see for example Photosynth Res. 2005 June; 84(1-3):21-7).

The number of photons striking a culture of microalgae cells can be manipulated, as well as other parameters such as the wavelength spectrum and ratio of dark:light hours per day. Microalgae can also be cultured in natural light, as well as simultaneous and/or alternating combinations of natural light and artificial light. For example, microalgae can be cultured under natural light during daylight hours and under artificial light during night hours.

In one aspect of the invention, a microorganism is exposed to about 0.1% to about 1% of light irradiance required for photosynthesis, preferably about 0.3% to about 0.8% of light irradiance required for photosynthesis by the organism. Typical light irradiance can be between 0.1-300 $\mu$mol photons m$^{-2}$ s$^{-1}$ including less than 0.1, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51 to 99, 100, 101 to 149, 150, 151, to 199, 200, 201 to 249, 250, or greater than 250 $\mu$mol photons m$^{-2}$ s$^{-1}$. Light irradiance can be about 0.01-1 $\mu$mol photons m$^{-2}$ s$^{-1}$, preferably between 1-10 $\mu$mol photons m$^{-2}$ s$^{-1}$, or between 10-100 $\mu$mol photons m$^{-2}$ s$^{-1}$, or between 100-300 $\mu$mol photons m$^{-2}$ s$^{-1}$, or between 100-300 $\mu$mol photons m$^{-2}$ s$^{-1}$. Also included are light irradiances between the above noted light irradiances, e.g., 1.1, 2.1, 2.5, or 3.5 $\mu$mol photons m$^2$ s$^{-1}$.

In one aspect, different light spectrums (e.g. 360-700 nm) can be used. Light spectrums can be less than 300, 300, 350, 400, 450, 500, 550, 600, 650, 700, or 750 nm or more. Also included are light spectrums between the above noted light spectrums, e.g., 360 or 440 nm.

In one aspect, the irradiation can be applied in a continuous manner. In another aspect, the irradiation can be applied in a cyclic pattern with an appropriate period of lighting including but not limited to 12 h light:12 h dark or 16 h light:8 h dark. Light patterns can include less than 1, 1, 2, 3, 4, 5, 6, 7, 8, 9, 10, 11, 12, 13, 14, 15, 16, 17, 18, 19, 20, 21, 22, 23, or 24 h of light and/or less than 1, 1, 2, 3, 4, 5, 6, 7, 8, 9, 10, 11, 12, 13, 14, 15, 16, 17, 18, 19, 20, 21, 22, or 23 hours (h) of dark. Also included are light patterns between the above noted light patterns, e.g., 7.5 h of light or 7.5 h of dark.

In one aspect, the irradiation can be natural sunlight collected by a solar collector and transmitted to the interior of a bioreactor through an optical fiber.

In another aspect, artificial light, such as light emitted diodes (LEDs) or fluorescent light can be used as light source. In another aspect, natural sunlight and artificial light can be used together.

In one aspect, the irradiation is a full spectrum of light.

In another aspect, the irradiation is a specific wavelength of light or a range of spectrum light transmitted through a specific filter.

In one aspect, the methods disclosed herein can be performed in dark, without controlled illumination. In one aspect, the methods disclosed herein can be performed under normal illumination conditions. In one aspect, the methods disclosed herein can be performed without controlled illumination.

Methods of Recovering Lipids and Hydrocarbons

Hydrocarbons (e.g., lipids, fatty acids, aldehydes, alcohols, and alkanes) produced by cells of the invention can be harvested, or otherwise collected, by any convenient means. For example, hydrocarbons secreted from cells can be centrifuged to separate the hydrocarbons in a hydrophobic layer from contaminants in an aqueous layer and optionally from any solid materials as a precipitate in after centrifugation. Material containing cell or cell fractions can be treated with proteases to degrade contaminating proteins before or after centrifugation. In some instances the contaminating proteins are associated, possibly covalently, to hydrocarbons or hydrocarbon precursors which form hydrocarbons upon removal of the protein. In other instances the hydrocarbon molecules are in a preparation that also contains proteins. Proteases can be added to hydrocarbon preparations containing proteins to degrade proteins (for example, the protease from *Streptomyces griseus* can be used (SigmaAldrich catalog number P5147). After digestion, the hydrocarbons are preferably purified from residual proteins, peptide fragments, and amino acids. This purification can be accomplished, for example, by methods listed above such as centrifugation and filtration.

Extracellular hydrocarbons can also be extracted in vivo from living microalgae cells which are then returned to a bioreactor by exposure of the cells, in an otherwise sterile environment, to a non-toxic extraction solvent, followed by separation of the living cells and the hydrophobic fraction of extraction solvent and hydrocarbons, wherein the separated living cells are then returned to a culture container such as a stainless steel fermentor or photobioreactor (see Biotechnol Bioeng. 2004 Dec. 5; 88(5):593-600 and Biotechnol Bioeng. 2004 Mar. 5; 85(5):475-81).

Hydrocarbons can also be isolated by whole cell extraction. The cells are first disrupted and then intracellular and cell membrane/cell wall-associated hydrocarbons as well as extracellular hydrocarbons can be collected from the whole cell mass, such as by use of centrifugation as described above.

Various methods are available for separating hydrocarbons and lipids from cellular lysates produced by the above methods. For example, hydrocarbons can be extracted with a hydrophobic solvent such as hexane (see Frenz et al. 1989, Enzyme Microb. Technol., 11:717). Hydrocarbons can also be extracted using liquefaction (see for example Sawayama et al. 1999, Biomass and Bioenergy 17:33-39 and Inoue et al. 1993, Biomass Bioenergy 6(4):269-274); oil liquefaction (see for example Minowa et al. 1995, Fuel 74(12):1735-1738); and supercritical $CO_2$ extraction (see for example Mendes et al. 2003, Inorganica Chimica Acta 356:328-334).

Miao and Wu describe a protocol of the recovery of microalgal lipid from a culture in which the cells were harvested by centrifugation, washed with distilled water and dried by freeze drying. The resulting cell powder was pulverized in a mortor and then extracted with n-hexane. Miao and Wu, Biosource Technology (2006) 97:841-846.

Lysing Cells

Intracellular lipids and hydrocarbons produced in microorganisms are, in some aspects, extracted after lysing the cells of the microorganism. Once extracted, the lipids and/or hydrocarbons can be further refined to produce, e.g., oils, fuels, or oleochemicals.

After completion of culturing, the microorganisms can be separated from the fermentation broth. Optionally, the separation is effected by centrifugation to generate a concentrated paste. Centrifugation does not remove significant amounts of intracellular water from the microorganisms and is not a drying step. The biomass can then be washed with a washing solution (e.g., DI water) to get rid of the fermentation broth and debris. Optionally, the washed microbial biomass can also be dried (oven dried, lyophilized, etc.) prior to cell disruption. Alternatively, cells can be lysed without separation from some or all of the fermentation broth when the fermentation is complete. For example, the cells can be at a ratio of less than 1:1 v:v cells to extracellular liquid when the cells are lysed.

Microorganisms containing a lipid and/or hydrocarbon can be lysed to produce a lysate. As detailed herein, the step of lysing a microorganism (also referred to as cell lysis) can be achieved by any convenient means, including heat-induced lysis, adding a base, adding an acid, using enzymes such as proteases and polysaccharide degradation enzymes such as amylases, using ultrasound, mechanical lysis, using osmotic shock, infection with a lytic virus, and/or expression of one or more lytic genes. Lysis is performed to release intracellular molecules which have been produced by the microorganism. Each of these methods for lysing a microorganism can be used as a single method or in combination simultaneously or sequentially.

The extent of cell disruption can be observed by microscopic analysis. Using one or more of the methods described herein, typically more than 70% cell breakage is observed. Preferably, cell breakage is more than 80%, more preferably more than 90% and most preferred about 100%.

In particular aspects, the microorganism is lysed after growth, for example to increase the exposure of cellular lipid and/or hydrocarbon for extraction or further processing. The timing of lipase expression (e.g., via an inducible promoter) or cell lysis can be adjusted to optimize the yield of lipids and/or hydrocarbons. Below are described a number of lysis techniques. These techniques can be used individually or in combination.

Heat-Induced Lysis

In a preferred aspect of the present invention, the step of lysing a microorganism comprises heating of a cellular suspension containing the microorganism. In this aspect, the fermentation broth containing the microorganisms (or a suspension of microorganisms isolated from the fermentation broth) is heated until the microorganisms, i.e., the cell walls and membranes of microorganisms degrade or breakdown. Typically, temperatures applied are at least 50 C. Higher temperatures, such as, at least 30 C, at least 60 C, at least 70 C, at least 80 C, at least 90 C, at least 100 C, at least 110 C, at least 120 C, at least 130 C or higher are used for more efficient cell lysis.

Lysing cells by heat treatment can be performed by boiling the microorganism. Alternatively, heat treatment (without boiling) can be performed in an autoclave. The heat treated lysate can be cooled for further treatment.

Cell disruption can also be performed by steam treatment, i.e., through addition of pressurized steam. Steam treatment of microalgae for cell disruption is described, for example, in U.S. Pat. No. 6,750,048.

Lysis Using a Base

In another preferred aspect of the present invention, the step of lysing a microorganism comprises adding a base to a cellular suspension containing the microorganism.

The base should be strong enough to hydrolyze at least a portion of the proteinaceous compounds of the microorganisms used. Bases which are useful for solubilizing proteins are known in the art of chemistry. Exemplary bases which are useful in the methods of the present invention include, but are not limited to, hydroxides, carbonates and bicarbonates of lithium, sodium, potassium, calcium, and mixtures thereof. A preferred base is KOH. Base treatment of microalgae for cell disruption is described, for example, in U.S. Pat. No. 6,750,048.

Acidic Lysis

In another preferred aspect of the present invention, the step of lysing a microorganism comprises adding an acid to a cellular suspension containing the microorganism. Acid lysis can be affected using an acid at a concentration of 10-500 mN or preferably 40-160 nM. Acid lysis is preferably performed at above room temperature (e.g., at 40-160, and preferably a temperature of 50-130. For moderate temperatures (e.g., room temperature to 100 C and particularly room temperature to 65, acid treatment can usefully be combined with sonication or other cell disruption methods.

Lysing Cells Using Enzymes

In another preferred aspect of the present invention, the step of lysing a microorganism comprises lysing the microorganism by using an enzyme. Preferred enzymes for lysing a microorganism are proteases and polysaccharide-degrading enzymes such as hemicellulase (e.g., hemicellulase from *Aspergillus niger*; Sigma Aldrich, St. Louis, Mo.; #H2125), pectinase (e.g., pectinase from *Rhizopus* sp.; Sigma Aldrich, St. Louis, Mo.; #P2401), Mannaway 4.0 L (Novozymes), cellulase (e.g., cellulose from *Trichoderma viride*; Sigma Aldrich, St. Louis, Mo.; #C9422), and driselase (e.g., driselase from *Basidiomycetes* sp.; Sigma Aldrich, St. Louis, Mo.; #D9515.

Cellulases

In a preferred aspect of the present invention, a cellulase for lysing a microorganism is a polysaccharide-degrading enzyme, optionally from *Chlorella* or a *Chlorella* virus.

Proteases

Proteases such as *Streptomyces griseus* protease, chymotrypsin, proteinase K, proteases listed in Degradation of Polylactide by Commercial Proteases, Oda Y et al., Journal of Polymers and the Environment, Volume 8, Number 1, January 2000, pp. 29-32(4), and other proteases can be used to lyse microorganisms. Other proteases that can be used include Alcalase 2.4 FG (Novozymes) and Flavourzyme 100 L (Novozymes).

Combinations

Any combination of a protease and a polysaccharide-degrading enzyme can also be used, including any combination of the preceding proteases and polysaccharide-degrading enzymes.

Lysing Cells Using Ultrasound

In another preferred aspect of the present invention, the step of lysing a microorganism is performed by using ultrasound, i.e., sonication. Thus, cells can also by lysed with high frequency sound. The sound can be produced electronically and transported through a metallic tip to an appropriately concentrated cellular suspension. This sonication (or ultrasonication) disrupts cellular integrity based on the creation of cavities in cell suspension.

Mechanical Lysis

In another preferred aspect of the present invention, the step of lysing a microorganism is performed by mechanical lysis. Cells can be lysed mechanically and optionally homogenized to facilitate hydrocarbon (e.g., lipid) collection. For example, a pressure disrupter can be used to pump a cell containing slurry through a restricted orifice valve. High pressure (up to 1500 bar) is applied, followed by an instant expansion through an exiting nozzle. Cell disruption is accomplished by three different mechanisms: impingement on the valve, high liquid shear in the orifice, and sudden pressure drop upon discharge, causing an explosion of the cell. The method releases intracellular molecules.

Alternatively, a ball mill can be used. In a ball mill, cells are agitated in suspension with small abrasive particles, such as beads. Cells break because of shear forces, grinding between beads, and collisions with beads. The beads disrupt the cells to release cellular contents. Cells can also be disrupted by shear forces, such as with the use of blending (such as with a high speed or Waring blender as examples), the french press, or even centrifugation in case of weak cell walls, to disrupt cells.

Lysing Cells By Osmotic Shock (Cytolysis)

In another preferred aspect of the present invention, the step of lysing a microorganism is performed by applying an osmotic shock.

Infection With A Lytic Virus

In a preferred aspect of the present invention, the step of lysing a microorganism comprises infection of the microorganism with a lytic virus. A wide variety of viruses are known to lyse microorganisms suitable for use in the present invention, and the selection and use of a particular lytic virus for a particular microorganism is within the level of skill in the art.

For example, paramecium bursaria chlorella virus (PBCV-1) is the prototype of a group (family Phycodnaviridae, genus *Chlorovirus*) of large, icosahedral, plaque-forming, double-stranded DNA viruses that replicate in, and lyse, certain unicellular, eukaryotic *chlorella*-like green algae. Accordingly, any susceptible microalgae can be lysed by infecting the culture with a suitable *chlorella* virus. See for example Adv. Virus Res. 2006; 66:293-336; Virology, 1999 Apr. 25; 257(1):15-23; Virology, 2004 Jan. 5; 318(1):214-23; Nucleic Acids Symp. Ser. 2000; (44):161-2; J. Virol. 2006 March; 80(5):2437-44; and Annu. Rev. Microbiol. 1999; 53:447-94.

Autolysis (Expression of a Lytic Gene)

In another preferred aspect of the present invention, the step of lysing a microorganism comprises autolysis. In this aspect, a microorganism according to the invention is genetically engineered to produce a lytic protein that will lyse the microorganism. This lytic gene can be expressed using an inducible promoter so that the cells can first be grown to a desirable density in a fermentor, followed by induction of the promoter to express the lytic gene to lyse the cells. In one aspect, the lytic gene encodes a polysaccharide-degrading enzyme.

In certain other aspects, the lytic gene is a gene from a lytic virus. Thus, for example, a lytic gene from a *Chlorella* virus can be expressed in an algal cell of the genus *Chlorella*, such as *C. protothecoides*.

Suitable expression methods are described herein with respect to the expression of a lipase gene. Expression of lytic genes is preferably done using an inducible promoter, such as a promoter active in microalgae that is induced by a stimulus such as the presence of a small molecule, light, heat, and other stimuli. For example, see Virology 260, 308-315 (1999); FEMS Microbiology Letters 180 (1999) 45-53; Virology 263, 376-387 (1999); and Virology 230, 361-368 (1997).

Extraction of Lipids and Hydrocarbons

Lipids and hydrocarbons generated by the microorganisms of the present invention can be recovered by extraction with an organic solvent. In some cases, the preferred organic solvent is hexane. Typically, the organic solvent is added directly to the lysate without prior separation of the lysate components. In one aspect, the lysate generated by one or more of the methods described above is contacted with an organic solvent for a period of time sufficient to allow the lipid and/or hydrocarbon components to form a solution with the organic solvent. In some cases, the solution can then be further refined to recover specific desired lipid or hydrocarbon components. Hexane extraction methods are well known in the art.

Methods of Processing Lipids and Hydrocarbons

Enzymatic Modification

Hydrocarbons (e.g., lipids, fatty acids, aldehydes, alcohols, and alkanes) produced by cells as described herein can be modified by the use of one or more enzymes, including a lipase. When the hydrocarbons are in the extracellular environment of the cells, the one or more enzymes can be added to that environment under conditions in which the enzyme modifies the hydrocarbon or completes its synthesis from a hydrocarbon precursor. Alternatively, the hydrocarbons can be partially, or completely, isolated from the cellular material before addition of one or more catalysts such as enzymes. Such catalysts are exogenously added, and their activity occurs outside the cell or in vitro.

Thermal and Other Catalytic Modification

Hydrocarbons produced by cells in vivo, or enzymatically modified in vitro, as described herein can be optionally further processed by conventional means. The processing can include "cracking" to reduce the size, and thus increase the hydrogen:carbon ratio, of hydrocarbon molecules. Catalytic and thermal cracking methods are routinely used in hydrocarbon and triglyceride oil processing. Catalytic methods involve the use of a catalyst, such as a solid acid catalyst. The catalyst can be silica-alumina or a zeolite, which result in the heterolytic, or asymmetric, breakage of a carbon-carbon bond to result in a carbocation and a hydride anion. These reactive intermediates then undergo either rearrangement or hydride transfer with another hydrocarbon. The reactions can thus regenerate the intermediates to result in a self-propagating chain mechanism. Hydrocarbons can also be processed to reduce, optionally to zero, the number of carbon-carbon double, or triple, bonds therein. Hydrocarbons can also be processed to remove or eliminate a ring or cyclic structure therein. Hydrocarbons can also be processed to increase the hydrogen:carbon ratio. This can include the addition of hydrogen ("hydrogenation") and/or the "cracking" of hydrocarbons into smaller hydrocarbons.

Thermal methods involve the use of elevated temperature and pressure to reduce hydrocarbon size. An elevated temperature of about 800 C. and pressure of about 700 kPa can be used. These conditions generate "light," a term that is sometimes used to refer to hydrogen-rich hydrocarbon molecules (as distinguished from photon flux), while also generating, by condensation, heavier hydrocarbon molecules which are relatively depleted of hydrogen. The methodology provides homolytic, or symmetrical, breakage and produces alkenes, which can be optionally enzymatically saturated as described above.

Catalytic and thermal methods are standard in plants for hydrocarbon processing and oil refining. Thus hydrocarbons produced by cells as described herein can be collected and processed or refined via conventional means. See Hillen et al. (Biotechnology and Bioengineering, Vol. XXIV: 193-205 (1982)) for a report on hydrocracking of microalgae-produced hydrocarbons. In alternative aspects, the fraction is treated with another catalyst, such as an organic compound, heat, and/or an inorganic compound. For processing of lipids into biodiesel, a transesterification process is used as described in Section IV herein.

Hydrocarbons produced via methods of the present invention are useful in a variety of industrial applications. For example, the production of linear alkylbenzene sulfonate (LAS), an anionic surfactant used in nearly all types of detergents and cleaning preparations, utilizes hydrocarbons generally comprising a chain of 10-14 carbon atoms. See, for example, U.S. Pat. Nos. 6,946,430; 5,506,201; 6,692,730; 6,268,517; 6,020,509; 6,140,302; 5,080,848; and 5,567,359. Surfactants, such as LAS, can be used in the manufacture of personal care compositions and detergents, such as those described in U.S. Pat. Nos. 5,942,479; 6,086,903; 5,833,999; 6,468,955; and 6,407,044.

Methods of Producing Fuels Suitable for Use in Diesel Vehicles and Jet Engines

Increasing interest is directed to the use of hydrocarbon components of biological origin in fuels, such as biodiesel, renewable diesel, and jet fuel, since renewable biological starting materials that can replace starting materials derived from fossil fuels are available, and the use thereof is desirable. There is a need for methods for producing hydrocarbon components from biological materials. The present invention fulfills this need by providing methods for production of biodiesel, renewable diesel, and jet fuel using the lipids generated by the methods described herein as a biological material to produce biodiesel, renewable diesel, and jet fuel.

Traditional diesel fuels are petroleum distillates rich in paraffinic hydrocarbons. They have boiling ranges as broad as 370 to 780 F, which are suitable for combustion in a compression ignition engine, such as a diesel engine vehicle. The American Society of Testing and Materials (ASTM) establishes the grade of diesel according to the boiling range, along with allowable ranges of other fuel properties, such as cetane number, cloud point, flash point, viscosity, aniline point, sulfur content, water content, ash content, copper strip corrosion, and carbon residue. Technically, any hydrocarbon distillate material derived from biomass or otherwise that meets the appropriate ASTM specification can be defined as diesel fuel (ASTM D975), jet fuel (ASTM D1655), or as biodiesel (ASTM D6751).

After extraction, lipid and/or hydrocarbon components recovered from the microbial biomass described herein can be subjected to chemical treatment to manufacture a fuel for use in diesel vehicles and jet engines.

Biodiesel

Biodiesel is a liquid which varies in color—between golden and dark brown—depending on the production feedstock. It is practically immiscible with water, has a high boiling point and low vapor pressure. Biodiesel refers to a diesel-equivalent processed fuel for use in diesel-engine vehicles. Biodiesel is biodegradable and non-toxic. An additional benefit of biodiesel over conventional diesel fuel is lower engine wear.

Typically, biodiesel comprises C14-C18 alkyl esters. Various processes convert biomass or a lipid produced and isolated as described herein to diesel fuels. A preferred method to produce biodiesel is by transesterification of a lipid as described herein. A preferred alkyl ester for use as biodiesel is a methyl ester or ethyl ester.

Biodiesel produced by a method described herein can be used alone or blended with conventional diesel fuel at any concentration in most modern diesel-engine vehicles. When blended with conventional diesel fuel (petroleum diesel), biodiesel can be present from about 0.1% to about 99.9%. Much of the world uses a system known as the "B" factor to state the amount of biodiesel in any fuel mix. For example, fuel containing 20% biodiesel is labeled B20. Pure biodiesel is referred to as B100.

Biodiesel can also be used as a heating fuel in domestic and commercial boilers. Existing oil boilers can contain rubber parts and can require conversion to run on biodiesel. The conversion process is usually relatively simple, involving the exchange of rubber parts for synthetic parts due to biodiesel being a strong solvent. Due to its strong solvent power, burning biodiesel will increase the efficiency of boilers.

Biodiesel can be used as an additive in formulations of diesel to increase the lubricity of pure Ultra-Low Sulfur Diesel (ULSD) fuel, which is advantageous because it has virtually no sulfur content.

Biodiesel is a better solvent than petrodiesel and can be used to break down deposits of residues in the fuel lines of vehicles that have previously been run on petrodiesel.

Production of Biodiesel

Biodiesel can be produced by transesterification of triglycerides contained in oil-rich biomass. Thus, in another aspect of the present invention a method for producing biodiesel is provided. In a preferred aspect, the method for producing biodiesel comprises the steps of (a) cultivating a lipid-containing microorganism using methods disclosed herein (b) lysing a lipid-containing microorganism to produce a lysate, (c) isolating lipid from the lysed microorganism, and (d) transesterifying the lipid composition, whereby biodiesel is produced.

Methods for growth of a microorganism, lysing a microorganism to produce a lysate, treating the lysate in a medium comprising an organic solvent to form a heterogeneous mixture and separating the treated lysate into a lipid composition have been described above and can also be used in the method of producing biodiesel.

Lipid compositions can be subjected to transesterification to yield long-chain fatty acid esters useful as biodiesel. Preferred transesterification reactions are outlined below and include base catalyzed transesterification and transesterification using recombinant lipases.

In a base-catalyzed transesterification process, the triacylglycerides are reacted with an alcohol, such as methanol or ethanol, in the presence of an alkaline catalyst, typically potassium hydroxide. This reaction forms methyl or ethyl esters and glycerin (glycerol) as a byproduct.

General Chemical Process

Animal and plant oils are typically made of triglycerides which are esters of free fatty acids with the trihydric alcohol, glycerol. In transesterification, the glycerol in a triacylglyceride (TAG) is replaced with a short-chain alcohol such as methanol or ethanol.

Using Recombinant Lipases

Transesterification has also been carried out experimentally using an enzyme, such as a lipase instead of a base. Lipase-catalyzed transesterification can be carried out, for example, at a temperature between the room temperature and 80 C, and a mole ratio of the TAG to the lower alcohol of greater than 1:1, preferably about 3:1.

Lipases suitable for use in transesterification are found in, e.g. U.S. Pat. Nos. 4,798,793; 4,940,845 5,156,963; 5,342,768; 5,776,741 and WO89/01032.

One challenge to using a lipase for the production of fatty acid esters suitable for biodiesel is that the price of lipase is much higher than the price of sodium hydroxide (NaOH) used by the strong base process. This challenge has been addressed by using an immobilized lipase, which can be recycled. However, the activity of the immobilized lipase must be maintained after being recycled for a minimum number of cycles to allow a lipase-based process to compete with the strong base process in terms of the production cost. Immobilized lipases are subject to poisoning by the lower alcohols typically used in transesterification. U.S. Pat. No. 6,398,707 (issued Jun. 4, 2002 to Wu et al.) describes methods for enhancing the activity of immobilized lipases and regenerating immobilized lipases having reduced activity.

In particular aspects, a recombinant lipase is expressed in the same microorganisms that produce the lipid on which the lipase acts. DNA encoding the lipase and selectable marker is preferably codon-optimized cDNA. Methods of recoding genes for expression in microalgae are described in U.S. Pat. No. 7,135,290.

Standards

The common international standard for biodiesel is EN 14214. ASTM D6751 is the most common biodiesel standard referenced in the United States and Canada. Germany uses DIN EN 14214 and the UK requires compliance with BS EN 14214.

Basic industrial tests to determine whether the products conform to these standards typically include gas chromatography, HPLC, and others. Biodiesel meeting the quality standards is very non-toxic, with a toxicity rating ($LD_{50}$) of greater than 50 mL/kg.

Renewable Diesel

Renewable diesel comprises alkanes, such as C16:0 and C18:0 and thus, are distinguishable from biodiesel. High quality renewable diesel conforms to the ASTM D975 standard.

The lipids produced by the methods of the present invention can serve as feedstock to produce renewable diesel. Thus, in another aspect of the present invention, a method for producing renewable diesel is provided. Renewable diesel can be produced by at least three processes: hydrothermal processing (hydrotreating); hydroprocessing; and indirect liquefaction. These processes yield non-ester distillates. During these processes, triacylglycerides produced and isolated as described herein, are converted to alkanes.

In a preferred aspect, the method for producing renewable diesel comprises (a) cultivating a lipid-containing microorganism using methods disclosed herein (b) lysing the microorganism to produce a lysate, (c) isolating lipid from the lysed microorganism, and (d) deoxygenating and hydrotreating the lipid to produce an alkane, whereby renewable diesel is produced. Lipids suitable for manufacturing renewable diesel can be obtained via extraction from microbial biomass using an organic solvent such as hexane, or via other methods, such as those described in U.S. Pat. No. 5,928,696.

In some methods, the microbial lipid is first cracked in conjunction with hydrotreating to reduce carbon chain length and saturate double bonds, respectively. The material is then isomerized, also in conjunction with hydrotreating. The naptha fraction can then be removed through distillation, followed by additional distillation to vaporize and distill components desired in the diesel fuel to meet a D975 standard while leaving components that are heavier than desired for meeting a D 975 standard. Hydrotreating, hydrocracking, deoxygenation and isomerization methods of chemically modifying oils, including triglyceride oils, are well known in the art. See for example European patent applications EP1741768 (A1); EP1741767 (A1); EP1682466 (A1); EP1640437 (A1); EP1681337 (A1); EP1795576 (A1); and U.S. Pat. Nos. 7,238,277; 6,630,066; 6,596,155; 6,977,322; 7,041,866; 6,217,746; 5,885,440; 6,881,873.

Hydrotreating

In a preferred aspect of the method for producing renewable diesel, treating the lipid to produce an alkane is performed by hydrotreating of the lipid composition. In hydrothermal processing, typically, biomass is reacted in water at an elevated temperature and pressure to form oils and residual solids. Conversion temperatures are typically 300 to 660 F, with pressure sufficient to keep the water primarily as a liquid, 100 to 170 standard atmosphere (atm). Reaction times are on the order of 15 to 30 minutes. After the reaction is completed, the organics are separated from the water. Thereby a distillate suitable for diesel is produced.

Hydroprocessing

A renewable diesel, referred to as "green diesel," can be produced from fatty acids by traditional hydroprocessing technology. The triglyceride-containing oils can be hydroprocessed either as co-feed with petroleum or as a dedicated feed. The product is a diesel fuel that conforms to the ASTM D975 specification. Thus, in another preferred aspect of the method for producing renewable diesel, treating the lipid composition to produce an alkane is performed by hydroprocessing of the lipid composition.

In some methods of making renewable diesel, the first step of treating a triglyceride is hydroprocessing to saturate double bonds, followed by deoxygenation at elevated temperature in the presence of hydrogen and a catalyst. In some methods, hydrogenation and deoxygenation occur in the same reaction. In other methods deoxygenation occurs before hydrogenation. Isomerization is then optionally performed, also in the presence of hydrogen and a catalyst. Naphtha components are preferably removed through distillation. For examples, see U.S. Pat. No. 5,475,160 (hydrogenation of triglycerides); U.S. Pat. No. 5,091,116 (deoxygenation, hydrogenation and gas removal); U.S. Pat. No. 6,391,815 (hydrogenation); and U.S. Pat. No. 5,888,947 (isomerization).

Petroleum refiners use hydroprocessing to remove impurities by treating feeds with hydrogen. Hydroprocessing conversion temperatures are typically 300 to 700 F. Pressures are typically 40 to 100 atm. The reaction times are typically on the order of 10 to 60 minutes.

Solid catalysts are employed to increase certain reaction rates, improve selectivity for certain products, and optimize hydrogen consumption.

Hydrotreating and hydroprocessing ultimately lead to a reduction in the molecular weight of the feed. In the case of triglyceride-containing oils, the triglyceride molecule is reduced to four hydrocarbon molecules under hydroprocessing conditions: a propane molecule and three heavier hydrocarbon molecules, typically in the C8 to C18 range.

Indirect Liquefaction

A traditional ultra-low sulfur diesel can be produced from any form of biomass by a two-step process. First, the biomass is converted to a syngas, a gaseous mixture rich in hydrogen and carbon monoxide. Then, the syngas is catalytically converted to liquids. Typically, the production of liquids is accomplished using Fischer-Tropsch (FT) synthesis. This technology applies to coal, natural gas, and heavy oils. Thus, in yet another preferred aspect of the method for producing renewable diesel, treating the lipid composition to produce an alkane is performed by indirect liquefaction of the lipid composition.

Jet Fuel

Aeroplane fuel is clear to straw colored. The most common fuel is an unleaded/paraffin oil-based fuel classified as Aeroplane A-1, which is produced to an internationally standardized set of specifications. Aeroplane fuel is a mixture of a large number of different hydrocarbons, possibly as many as a thousand or more. The range of their sizes (molecular weights or carbon numbers) is restricted by the requirements for the product, for example, freezing point or smoke point. Kerosone-type Aeroplane fuel (including Jet A and Jet A-1) has a carbon number distribution between about 8 and 16 carbon numbers. Wide-cut or naphta-type Aeroplane fuel (including Jet B) typically has a carbon number distribution between about 5 and 15 carbons.

Both Aeroplanes (Jet A and jet B) can contain a number of additives. Useful additives include, but are not limited to, antioxidants, antistatic agents, corrosion inhibitors, and fuel system icing inhibitor (FSII) agents. Antioxidants prevent gumming and usually, are based on alkylated phenols, for example, AO-30, AO-31, or AO-37. Antistatic agents dissipate static electricity and prevent sparking. Stadis 450 with dinonylnaphthylsulfonic acid (DINNSA) as the active ingredient is an example. Corrosion inhibitors, e.g., DCI-4A are used for civilian and military fuels and DCI-6A is used for military fuels. FSII agents, include, e.g., Di-EGME.

A solution is blending algae fuels with existing jet fuel. The present invention provides such a solution. The lipids produced by the methods of the present invention can serve as feedstock to produce jet fuel. Thus, in another aspect of the present invention, a method for producing jet fuel is provided. Herewith two methods for producing jet fuel from the lipids produced by the methods of the present invention are provided: fluid catalytic cracking (FCC); and hydrodeoxygenation (HDO).

Fluid Catalytic Cracking

Fluid Catalytic Cracking (FCC) is one method which is used to produce olefins, especially propylene from heavy crude fractions. There are reports in the literature that vegetable oils such as canola oil could be processed using FCC to give a hydrocarbon stream useful as a gasoline fuel.

The lipids produced by the method of the present invention can be converted to olefins. The process involves flowing the lipids produced through an FCC zone and collecting a product stream comprised of olefins, which is useful as a jet fuel. The lipids produced are contacted with a cracking catalyst at cracking conditions to provide a product stream comprising olefins and hydrocarbons useful as jet fuel.

In a preferred aspect, the method for producing jet fuel comprises (a) cultivating a lipid-containing microorganism using methods disclosed herein, (b) lysing the lipid-containing microorganism to produce a lysate, (c) isolating lipid from the lysate, and (d) treating the lipid composition, whereby jet fuel is produced.

In a preferred aspect of the method for producing a jet fuel, the lipid composition can be flowed through a fluid catalytic cracking zone, which, in one aspect, can comprise contacting the lipid composition with a cracking catalyst at cracking conditions to provide a product stream comprising $C_2$-$C_5$ olefins.

In certain aspects of this method it can be desirable to remove any contaminants that can be present in the lipid composition. Thus, prior to flowing the lipid composition through a fluid catalytic cracking zone, the lipid composition is pretreated. Pretreatment can involve contacting the lipid composition with an ion-exchange resin. The ion exchange resin is an acidic ion exchange resin, such as Amberlyst™-15 and can be used as a bed in a reactor through which the lipid composition is flowed, either upflow or downflow. Other pretreatments can include mild acid washes by contacting the lipid composition with an acid, such as sulfuric, acetic, nitric, or hydrochloric acid. Contacting is done with a dilute acid solution usually at ambient temperature and atmospheric pressure.

The lipid composition, optionally pretreated, is flowed to an FCC zone where the hydrocarbonaceous components are cracked to olefins. Catalytic cracking is accomplished by contacting the lipid composition in a reaction zone with a catalyst composed of finely divided particulate material. The reaction is catalytic cracking, as opposed to hydrocracking, and is carried out in the absence of added hydrogen or the consumption of hydrogen. As the cracking reaction proceeds, substantial amounts of coke are deposited on the catalyst. The catalyst is regenerated at high temperatures by burning coke from the catalyst in a regeneration zone. Coke-containing catalyst, referred to herein as "coked catalyst", is continually transported from the reaction zone to the regeneration zone to be regenerated and replaced by essentially coke-free regenerated catalyst from the regeneration zone. Fluidization of the catalyst particles by various gaseous streams allows the transport of catalyst between the reaction zone and regeneration zone. Methods for cracking hydrocarbons, such as those of the lipid composition described herein, in a fluidized stream of catalyst, transporting catalyst between reaction and regeneration zones, and combusting coke in the regenerator are well known by those skilled in the art of FCC processes. Exemplary FCC applications and catalysts useful for cracking the lipid composition to produce $C_2$-$C_5$ olefins are described in U.S. Pat. Nos. 6,538,169, 7,288,685, which are incorporated in their entirety by reference.

In one aspect, cracking the lipid composition of the present invention, takes place in the riser section or, alternatively, the lift section, of the FCC zone. The lipid composition is introduced into the riser by a nozzle resulting in the rapid vaporization of the lipid composition. Before contacting the catalyst, the lipid composition will ordinarily have a temperature of about 149 C to about 316 C (300 F to 600 F). The catalyst is flowed from a blending vessel to the riser where it contacts the lipid composition for a time of abort 2 seconds or less.

The blended catalyst and reacted lipid composition vapors are then discharged from the top of the riser through an outlet and separated into a cracked product vapor stream including olefins and a collection of catalyst particles covered with substantial quantities of coke and generally referred to as "coked catalyst." In an effort to minimize the contact time of the lipid composition and the catalyst which can promote further conversion of desired products to undesirable other products, any arrangement of separators such as a swirl arm arrangement can be used to remove coked catalyst from the product stream quickly. The separator, e.g. swirl arm separator, is located in an upper portion of a chamber with a stripping zone situated in the lower portion of the chamber. Catalyst separated by the swirl arm arrangement drops down into the stripping zone. The cracked product vapor stream comprising cracked hydrocarbons including light olefins and some catalyst exit the chamber via a conduit which is in communication with cyclones. The cyclones remove remaining catalyst particles from the product vapor stream to reduce particle concentrations to very low levels. The product vapor stream then exits the top of the separating vessel. Catalyst separated by the cyclones is returned to the separating vessel and then to the stripping zone. The stripping zone removes adsorbed hydrocarbons from the surface of the catalyst by counter-current contact with steam.

Low hydrocarbon partial pressure operates to favor the production of light olefins. Accordingly, the riser pressure is set at about 172 to 241 kPa (25 to 35 psia) with a hydrocarbon partial pressure of about 35 to 172 kPa (5 to 25 psia), with a preferred hydrocarbon partial pressure of about 69 to 138 kPa (10 to 20 psia). This relatively low partial pressure for hydrocarbon is achieved by using steam as a diluent to the extent that the diluent is 10 to 55 wt-% of lipid composition and preferably about 15 wt-% of lipid composition. Other diluents such as dry gas can be used to reach equivalent hydrocarbon partial pressures.

The temperature of the cracked stream at the riser outlet will be about 510 C. to 621 C (950 F to 1150 F). However, riser outlet temperatures above 566 C (1050 F) make more dry gas and more olefins. Whereas, riser outlet temperatures below 566 C (1050 F) make less ethylene and propylene. Accordingly, it is preferred to run the FCC process at a preferred temperature of about 566 C to about 630 C., preferred pressure of about 138 kPa to about 240 kPa (20 to 35 psia). Another condition for the process is the catalyst to lipid composition ratio which can vary from about 5 to about 20 and preferably from about 10 to about 15.

In one aspect of the method for producing a jet fuel, the lipid composition is introduced into the lift section of an FCC reactor. The temperature in the lift section will be very hot and range from about 700 C. (1292 F) to about 760 C. (1400 F) with a catalyst to lipid composition ratio of about 100 to about 150. It is anticipated that introducing the lipid composition into the lift section will produce considerable amounts of propylene and ethylene.

Gas and liquid hydrocarbon products produced can be analyzed by gas chromatography, HPLC, etc.

Hydrodeoxygenation

In another aspect of the method for producing a jet fuel using the lipid composition or the lipids produced as described herein, the structure of the lipid composition or the lipids is broken by a process referred to as hydrodeoxygenation (HDO).

HDO means removal of oxygen by means of hydrogen, that is, oxygen is removed while breaking the structure of the material. Olefinic double bonds are hydrogenated and any sulphur and nitrogen compounds are removed. Sulphur removal is called hydrodesulphurization (HDS). Pretreatment and purity of the raw materials (lipid composition or the lipids) contribute to the service life of the catalyst.

Generally in the HDO/HDS step, hydrogen is mixed with the feed stock (lipid composition or the lipids) and then the mixture is passed through a catalyst bed as a co-current flow, either as a single phase or a two phase feed stock. After the HDO/MDS step, the product fraction is separated and passed to a separate isomerzation reactor. An isomerization reactor for biological starting material is described in the literature (FI 100 248) as a co-current reactor.

The process for producing a fuel by hydrogenating a hydrocarbon feed, e.g., the lipid composition or the lipids herein, can also be performed by passing the lipid composition or the lipids as a co-current flow with hydrogen gas through a first hydrogenation zone, and thereafter the hydrocarbon effluent is further hydrogenated in a second hydrogenation zone by passing hydrogen gas to the second hydrogenation zone as a counter-current flow relative to the hydrocarbon effluent. Exemplary HDO applications and catalysts useful for cracking the lipid composition to produce $C_2$-$C_5$ olefins are described in U.S. Pat. No. 7,232,935, which is incorporated in its entirety by reference.

Typically, in the hydrodeoxygenation step, the structure of the biological component, such as the lipid composition or lipids herein, is decomposed, oxygen, nitrogen, phosphorus and sulphur compounds, and light hydrocarbons as gas are removed, and the olefinic bonds are hydrogenated. In the second step of the process, i.e. in the so-called isomerization step, isomerzation is carried out for branching the hydrocarbon chain and improving the performance of the paraffin at low temperatures.

In the first step i.e. HDO step of the cracking process, hydrogen gas and the lipid composition or lipids herein which are to be hydrogenated are passed to a HDO catalyst bed system either as co-current or counter-current flows, said catalyst bed system comprising one or more catalyst bed(s), preferably 1-3 catalyst beds. The HDO step is typically operated in a co-current manner. In case of a HDO catalyst bed system comprising two or more catalyst beds, one or more of the beds can be operated using the counter-current flow principle.

In the HDO step, the pressure varies between 20 and 150 bar, preferably between 50 and 100 bar, and the temperature varies between 200 and 500 C, preferably in the range of 300-400 C.

In the HDO step, known hydrogenation catalysts containing metals from Group VII and/or VIB of the Periodic System can be used. Preferably, the hydrogenation catalysts are supported Pd, Pt, Ni, NiMo or a CoMo catalysts, the support being alumina and/or silica. Typically, NiMo/$Al_2O_3$ and CoMo/$Al_2O_3$ catalysts are used.

Prior to the HDO step, the lipid composition or lipids herein can optionally be treated by prehydrogenation under milder conditions thus avoiding side reactions of the double bonds. Such prehydrogenation is carried out in the presence of a prehydrogenation catalyst at temperatures of 50 400 C and at hydrogen pressures of 1 200 bar, preferably at a temperature between 150 and 250 C and at a hydrogen pressure between 10 and 100 bar. The catalyst can contain metals from Group VIII and/or VIB of the Periodic System. Preferably, the prehydrogenation catalyst is a supported Pd, Pt, Ni, NiMo or a CoMo catalyst, the support being alumina and/or silica.

A gaseous stream from the HDO step containing hydrogen is cooled and then carbon monoxide, carbon dioxide, nitrogen, phosphorus and sulphur compounds, gaseous light hydrocarbons and other impurities are removed therefrom. After compressing, the purified hydrogen or recycled hydrogen is returned back to the first catalyst bed and/or between the catalyst beds to make up for the withdrawn gas stream. Water is removed from the condensed liquid. The liquid is passed to the first catalyst bed or between the catalyst beds.

After the HDO step, the product is subjected to an isomerization step. It is substantial for the process that the impurities are removed as completely as possible before the hydrocarbons are contacted with the isomerization catalyst. The isomerization step comprises an optional stripping step, wherein the reaction product from the HDO step can be purified by stripping with water vapour or a suitable gas such as light hydrocarbon, nitrogen or hydrogen. The optional stripping step is carried out in counter-current manner in a unit upstream of the isomerization catalyst, wherein the gas and liquid are contacted with each other, or before the actual isomerization reactor in a separate stripping unit utilizing counter-current principle.

After the stripping step the hydrogen gas and the hydrogenated lipid composition or lipids herein, and optionally an n-paraffin mixture, are passed to a reactive isomerization unit comprising one or several catalyst bed(s). The catalyst beds of the isomerization step can operate either in co-current or counter-current manner.

It is important for the process that the counter-current flow principle is applied in the isomerization step. In the isomerization step this is done by carrying out either the optional stripping step or the isomerization reaction step or both in counter-current manner.

The isomerization step and the HDO step can be carried out in the same pressure vessel or in separate pressure vessels. Optional prehydrogenation can be carried out in a separate pressure vessel or in the same pressure vessel as the HDO and isomerization steps.

In the isomerization step, the pressure varies in the range of 20 150 bar, preferably in the range of 20 100 bar, the temperature being between 200 and 500 C, preferably between 300 and 400 C.

In the isomerization step, isomerization catalysts known in the art can be used. Suitable isomerization catalysts contain molecular sieve and/or a metal from Group VII and/or a carrier. Preferably, the isomerization catalyst contains SAPO-11 or SAPO41 or ZSM-22 or ZSM-23 or ferrierite and Pt, Pd or N1 and $Al_2O_3$ or $SiO_2$. Typical isomerization catalysts are, for example, Pt/SAPO-11/$Al_2O_3$, Pt/ZSM-22/$Al_2O_3$, Pt/ZSM-23/$Al_2O_3$ and Pt/SAPO-11/$SiO_2$.

As the product, a high quality hydrocarbon component of biological origin, useful as a diesel fuel or a component thereof, is obtained, the density, cetane number and performance at low temperate of said hydrocarbon component being excellent.

Microbe Engineering

As noted above, in certain aspects of the present invention it is desirable to genetically modify a microorganism to enhance lipid production, modify the properties or proportions of components generated by the microorganism, or to improve or provide de novo growth characteristics on a variety of feedstock materials.

Promoters, cDNAs, and 3'UTRs, as well as other elements of the vectors, can be generated through cloning techniques using fragments isolated from native sources (see for example Molecular Cloning: A Laboratory Manual, Sambrook et al. (3d edition, 2001, Cold Spring Harbor Press; and U.S. Pat. No. 4,683,202). Alternatively, elements can be generated synthetically using known methods (see for example Gene. 1995 Oct. 16; 164(1):49-53). Microbial engineering methods are generally known in the art, e.g., U.S. Pat. App. No. 20090011480, herein incorporated by reference in its entirety, for all purposes.

EXAMPLES

Below are examples of specific aspects for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

The practice of the present invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, *Proteins: Structures and Molecular Properties* (W. H. Freeman and Company, 1993); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.); *Remington's Pharmaceutical Sciences*, 18th Edition (Easton, Pa.: Mack Publishing Company, 1990); Carey and Sundberg *Advanced Organic Chemistry* $3^{rd}$ *Ed.* (Plenum Press) Vols A and B(1992).

Example 1

Strains and Media

*Botryococcus braunii* race A strains UTEX 572 and UTEX 2441 were obtained from the algae culture collection at the University of Texas (Austin, Tex. USA). Initial cultures were grown separately in Erlenmeyer 250 ml flasks containing 120 ml modified BG11 medium with 2% glucose at 25° C. room temperature with aluminum foil loosely covering the flasks on an orbital shaker at 130 rpm under fluorescent lighting composed of two different bulbs (40 W natural sunshine and 40 W plant and aquarium fluorescent light bulbs). Modified BG11 medium contains following components per 1 L of deionized water: 17.6 mM NaNO3, 0.22 mM K2HPO4, 0.3 mM MgSO4 7H2O, 0.2 mM CaCl2 2H2O, 0.03 mM Citric acid H2O, 0.046 mM Ammonium Ferric Citrate, 0.002 mM Na2EDTA $2H_2O$, 0.18 mM Na2CO3, 1 ml of BG11 metal solution (2.86 g $H_3BO3$, 1.81 g MnCl2 4H2O, 0.22 g ZnSO4 7H2O, 0.39 g Na2MoO4 2H2O, 0.079 g CuSO4 5H2O, 49.4 mg Co(NO3)2 $6H_2O$ in 1 L deionized water), 10 mM HEPES, 0.5 g Casein Hydrolysate, and 1 ml of each of three vitamins (0.1 mM B12, 0.1 mM Biotin, 6.5 mM Thiamine dissolved separately in 50 mM HEPES pH7.8. Each vitamin solutions were filter sterilized before use). The final pH of the medium was adjusted to 7.8 with 20% KOH before autoclaving the medium. The vitamin solutions were added after autoclaving the medium. Once the initial culture reached a certain confluence, its concentration was measured by drying 5 ml of cell culture at 125° C. using a moisture analyzer (HG63 Mettler Toledo).

Experimental Procedure and Growth Measurement

Two liters of wastewater was obtained from Lion Raisins in Selma, Calif. The wastewater was derived from water used to wash dried grapes prior to packaging, which was the wastewater derived from the use of high pressure rinses, vacuums, and wash tanks. After a washing step, the wastewater usually contains about 2-4% glucose. The specific sample of wastewater used for this experiment contained 1.7% glucose. The wastewater was filtered with a 0.22 um filter system unit to sterilize it and pH was adjusted to 7.38 with 20% KOH. In one six-well plate (351146 Falcon), six different conditions were set up.
1. Wastewater (RW) only
2. Regular cell medium+2% glucose
3. Wastewater+NaNO3 (same concentrations as in #2)
4. Wastewater+other components in cell medium (same concentrations as in #2)
5. 50% wastewater (50% of wastewater+50% regular cell medium)
6. 25% wastewater (25% of wastewater+75% regular cell medium)

The final volume for each well was 6 ml. Initial cell concentration for each well was 0.5 mg/ml. Intensity of light was set at 3-5 $\mu mol/m^2 s^{-1}$ photons. The speed of the orbital shaker was set at 140 rpm. The experiment was carried out at room temperature for two weeks. At the end of the experimental period 1 ml of cell culture from each condition was transferred to pre measured eppendorf tubes, and they were spun down to obtain cell pellets. The cell pellets were freeze dried and the final dried cell weight was determined by subtracting the final weight of each eppendorf tube containing the dried cells to the initial eppendorf tube weight.

Results

Figure 2:
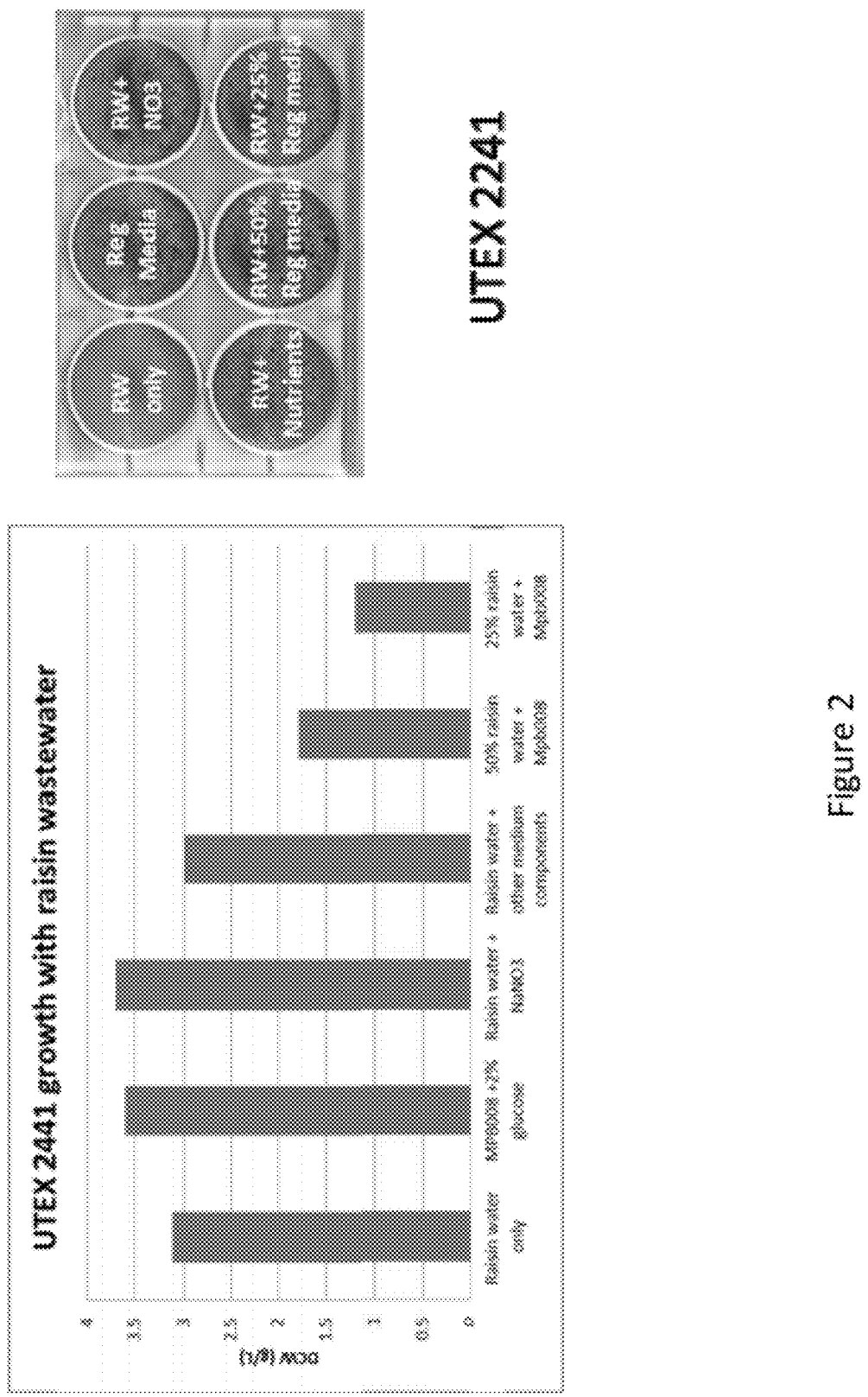
FIG. 2 shows the dry cell weight (DCW) of UTEX 2441 grown under different raisin wastewater conditions.
Figure 3:
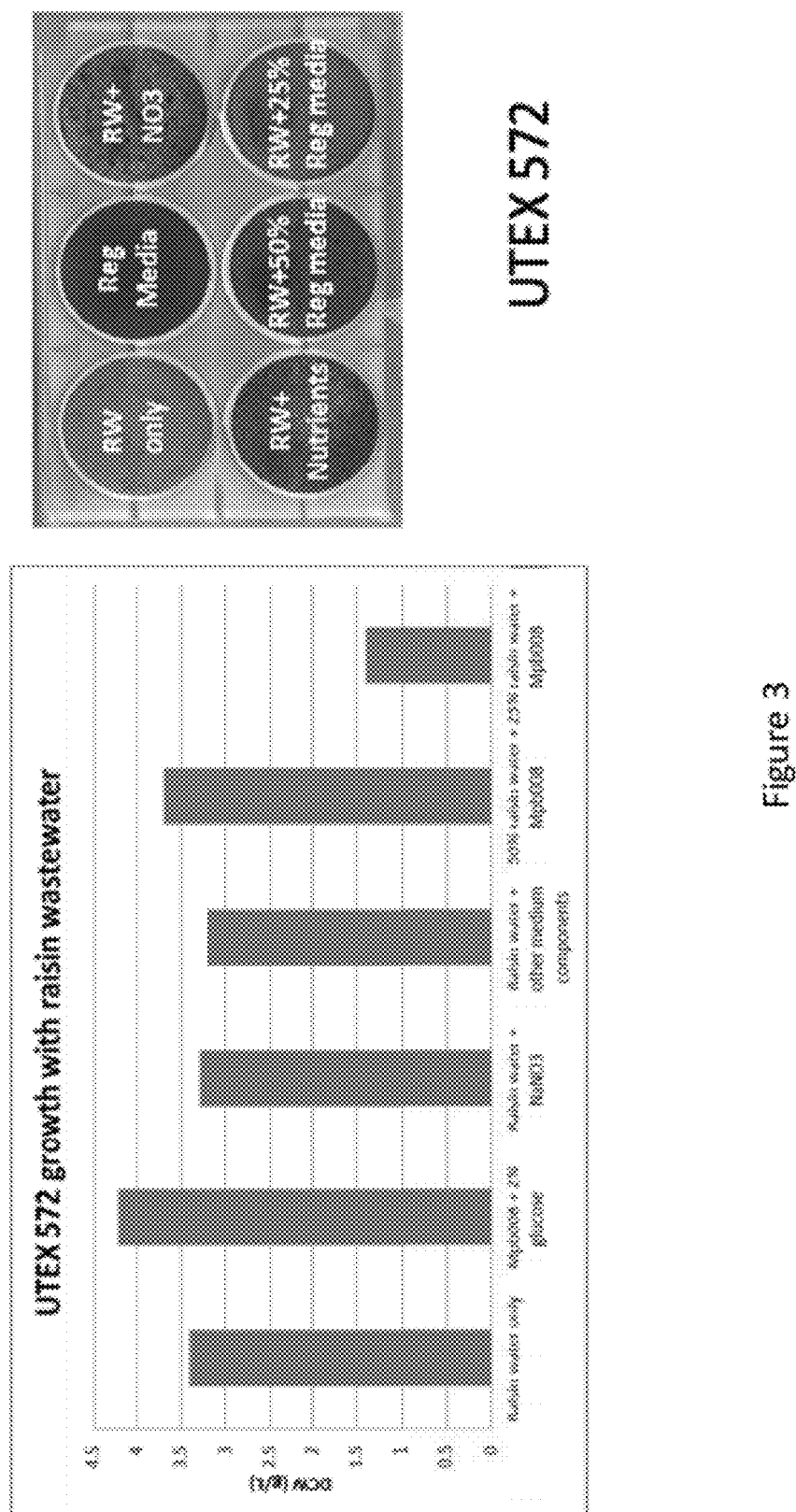
FIG. 3 shows the dry cell weight (DCW) of UTEX 572 grown under different raisin wastewater conditions.

As shown in FIG. 2, use of raisin wastewater resulted in growth of UTEX 2441 as measured by dry cell weight (DCW). As shown in FIG. 3, use of raisin wastewater resulted in growth of UTEX 572 as measured by dry cell weight (DCW).

Example 2

Strains and Media

*Neochloris oleabundans* UTEX 1185 was obtained from the culture collection of algae at the University of Texas (Austin, Tex. USA). Initial culture of the microalgae was grown in Erlenmeyer 250 ml flask containing 120 ml modified bold 3 N medium with 2% glucose at 25° C. room temperature with an aluminum foil loosely covering the flask on an orbital shaker at 130 rpm under alternating two 40 W natural sunshine (392316, Philips) and two 40 W plant and aquarium (392282, Philips) fluorescent light bulbs. Modified bold 3 N medium contains following components per 1 L of deionized water; 8.82 mM NaNO3, 0.43 mM K2HPO4, 0.3 mM MgSO4 7H2O, 0.17 mM CaCl2 2H2O, 1.29 mM KH2PO4, 0.43 mM NaCl, 6 ml of P—IV metal solution (0.75 g Na2EDTA 2H2O, 0.097 g FeCl3 6H2O, 0.041 g MnCl2 4H2O, 0.005 g ZnCl2, 0.002 g CoCl2 6H2O, 0.004 g Na2MoO4 2H2O in 1 L deionized water), 1 ml of each three vitamins (0.1 mM B12, 0.1 mM Biotin, 6.5 mM Thiamine dissolved separately in 50 mM HEPES pH7.8. Each vitamin solutions were filter sterilized before use). Final pH of the medium was adjusted to 7.5 with 20% KOH before autoclaving the medium. The vitamin solutions were added to cool down autoclaved medium. Once the initial culture reached certain confluence, its concentration was measured using optical density (OD) at 680 nm and 750 nm using Genesys 10 UV spectrophotometer (Thermo Scientific).

Experimental Procedure and Growth Measurement

Two liters of wastewater was obtained from Lion Raisins in Selma, Calif. The wastewater was derived from water used to wash dried grapes prior to packaging, which was the wastewater derived from the use of high pressure rinses, vacuums, and wash tanks. After washing step, the wastewater usually contains about 2-4% glucose. The specific sample wastewater used for this experiment contained 1.7% of glucose. The wastewater was filtered with 0.22 um filter system unit to sterilize and pH was adjusted to 7.38 with 20% KOH. In one six-well plate (351146 Falcon), six different conditions were set up.
1. Wastewater (RW) only
2. Regular cell medium+2% glucose
3. Wastewater+NaNO3 (same concentrations as in #2)

4. Wastewater+other components in cell medium (same concentrations as in #2)
5. 50% wastewater (50% of wastewater+50% regular cell medium)
6. 25% wastewater (25% of wastewater+75% regular cell medium)

Final volume for each well was 6 ml. Initial cell concentration for each well was O.D. 0.3 at 750 nm. Intensity of light was set at 3-5 μmol/m²s⁻¹ photons. The speed of the orbital shaker was set at 140 rpm. Experiment was carried out at room temperature for 4 days. At the end of experiment period 1 ml of cell culture from each condition was transferred to pre measured eppendorf tubes, and they were spun down to obtain cell pellets. The cell pellets were freeze dried and final dried cell weight was determined by subtracting final weight of eppendorf tube containing dried cell to initial eppendorf tube weight.

Results

Figure 4:
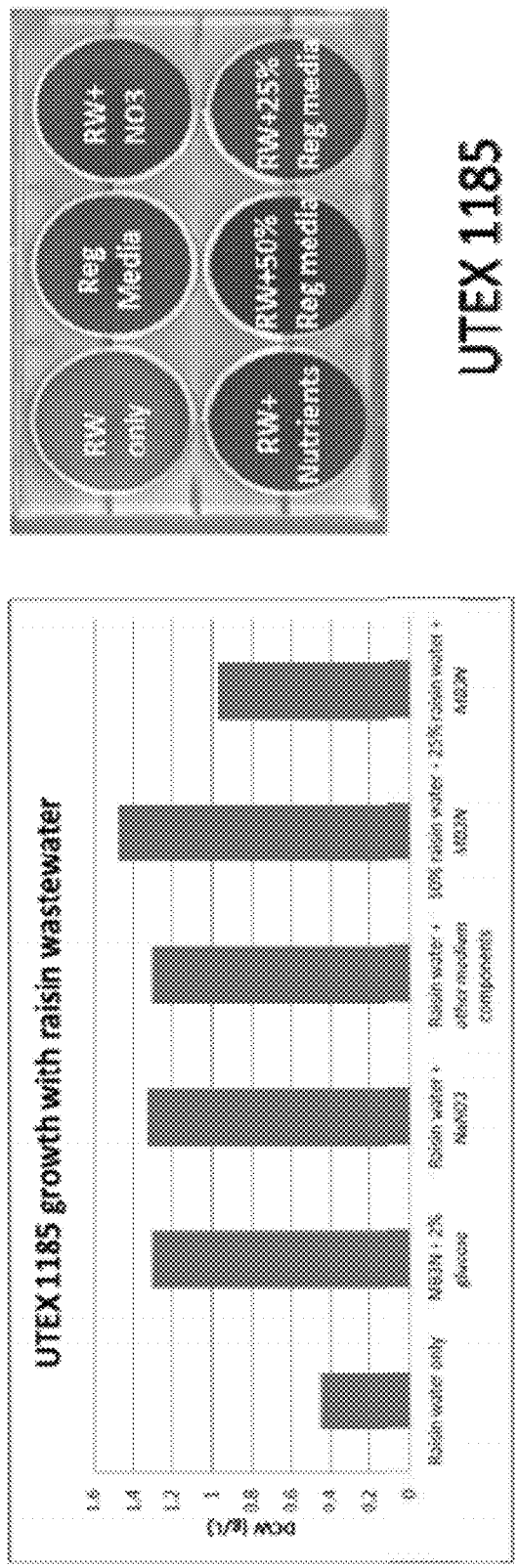
FIG. 4 shows the dry cell weight (DCW) of UTEX 1185 grown under different raisin wastewater conditions.

As shown in FIG. 4, use of raisin wastewater resulted in growth of UTEX 1185 as measured by dry cell weight (DCW).

Example 3

Strains and Media

*Botryococcus sudeticus* UTEX 2629 was obtained from the culture collection of algae at the University of Texas (Austin, Tex. USA). Initial culture was grown in Erlenmeyer 250 ml flask containing 120 ml modified BG11 medium with 2% glucose at 25° C. room temperature with an aluminum foil loosely covering the flask on an orbital shaker at 130 rpm under alternating two 40 W natural sunshine (392316, Philips) and two 40 W plant and aquarium (392282, Philips) fluorescent light bulbs. Modified BG11 medium contains following components per 1 L of deionized water; 17.6 mM NaNO3, 0.43 mM K2HPO4, 0.3 mM MgSO4 7H2O, 0.2 mM CaCl2 2H2O, 0.03 mM Citric acid H2O, 0.02 mM Ammonium Ferric Citrate, 0.002 mM Na2EDTA 2H$_2$O, 0.18 mM Na2CO3, 1 ml of BG11 metal solution (2.86 g H$_3$BO3, 1.81 g MnCl2 4H2O, 0.22 g ZnSO4 7H$_2$O, 0.39 g Na2MoO4 2H2O, 0.079 g CuSO4 5H$_2$O, 49.4 mg Co(NO3)2 6H2O in 1 L deionized water), 10 ml HEPES, 1 ml of each three vitamins (0.1 mM B12, 0.1 mM biotin, 6.5 mM thiamine dissolved separately in 50 mM HEPES pH7.8. Each vitamin solutions were filter sterilized before use). Final pH of the medium was adjusted to 7.8 with 20% KOH before autoclaving the medium. The vitamin solutions were added after autoclaving the medium. Once the initial culture reached certain confluence, its concentration was measured using optical density (OD at 680 nm and 750 nm) using Genesys 10 UV spectrophotometer (Thermo Scientific).

Experimental Procedure and Growth Measurement

Two liters of wastewater was obtained from Lion Raisins in Selma, Calif. The wastewater was derived from water used to wash dried grapes prior to packaging, which was the wastewater derived from the use of high pressure rinses, vacuums, and wash tanks. After washing step, the wastewater usually contains about 2-4% glucose. The specific sample wastewater used for this experiment contained 1.7% of glucose. The wastewater was filtered with 0.22 um filter system unit to sterilize and pH was adjusted to 7.38 with 20% KOH. In one six-well plate (351146 Falcon), six different conditions were set up.
1. Wastewater (RW) only
2. Regular cell medium+2% glucose
3. Wastewater+NaNO3 (same concentrations as in #2)

4. Wastewater+other components in cell medium (same concentrations as in #2)
5. 50% wastewater (50% of wastewater+50% regular cell medium)
6. 25% wastewater (25% of wastewater+75% regular cell medium)

Final volume for each well was 6 ml. Initial cell concentration for each well was O.D. 0.3 at 750 nm. Intensity of light was set at 3-5 μmol/m²s⁻¹ photons. The speed of the orbital shaker was set at 140 rpm. Experiment was carried out at room temperature for 4 days. At the end of experiment period 1 ml of cell culture from each condition was transferred to pre measured eppendorf tubes, and they were spun down to obtain cell pellets. The cell pellets were freeze dried and final dried cell weight was determined by subtracting final weight of eppendorf tube containing dried cell to initial eppendorf tube weight.

Results

Figure 5:
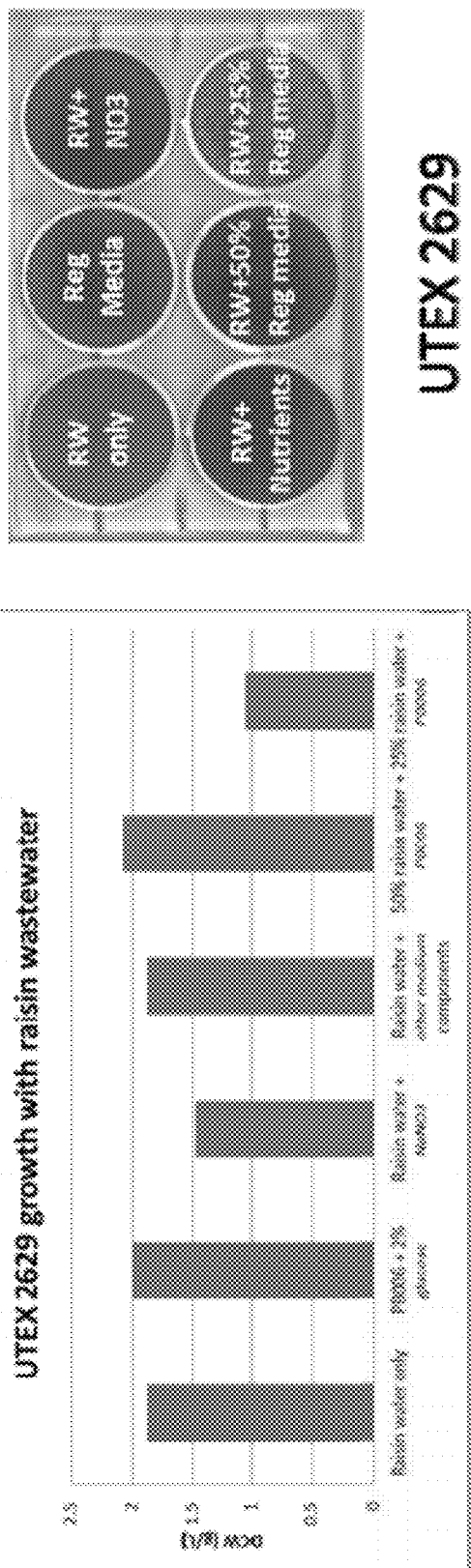
FIG. 5 shows the dry cell weight (DCW) of UTEX 2629 grown under different raisin wastewater conditions.

As shown in FIG. 5, use of raisin wastewater resulted in growth of UTEX 2629 as measured by dry cell weight (DCW).

Example 4

Strains and Media

*Neochloris oleabundans* UTEX 1185 was obtained from the culture collection of algae at the University of Texas (Austin, Tex. USA). Initial culture of the microalgae was grown in Erlenmeyer 250 ml flasks containing 120 ml modified bold 3 N medium with 2% glucose at 25° C. with aluminum foil loosely covering the flask on an orbital shaker at 130 rpm under alternating two 40 W natural sunshine (392316, Philips) and two 40 W plant and aquarium (392282, Philips) fluorescent light bulbs. Modified bold 3 N medium contained the following components per 1 L of deionized water: 8.82 mM NaNO3, 0.43 mM K2HPO4, 0.3 mM MgSO4 7H2O, 0.17 mM CaCl2 2H2O, 1.29 mM KH2PO4, 0.43 mM NaCl, 6 ml of P—IV metal solution (0.75 g Na2EDTA 2H2O, 0.097 g FeCl3 6H2O, 0.041 g MnCl2 4H2O, 0.005 g ZnCl2, 0.002 g CoCl2 6H2O, 0.004 g Na2MoO4 2H2O in 1 L deionized water), 1 ml of each of three vitamins (0.1 mM B12, 0.1 mM Biotin, 6.5 mM Thiamine dissolved separately in 50 mM HEPES pH7.8. Each vitamin solution was filter sterilized before use). Final pH of the medium was adjusted to 7.5 with 20% KOH before autoclaving the medium. The vitamin solutions were added to cool down the autoclaved medium. Once the initial culture reached a certain confluence, its concentration was measured by drying 5 ml of cell culture at 125° C. using a moisture analyzer (HG63 Mettler Toledo).

Experimental Procedure

Two liters of winery wastewater was obtained from Scheid Vineyards in Salinas, Calif. The wastewater was derived from: water used to wash grapes prior to processing, crushing, washing, tank disinfection, and filtering. After a washing step, the wastewater generally contained about 2-4% glucose. The specific sample of wastewater used for this experiment contained 1.7% to 1.9% glucose. One liter of wastewater was filtered with a 0.22 μm filter system unit to sterilize it and pH was adjusted to 7.5 with 20% KOH. Another one liter was autoclaved to sterilize it at 121° C. for 40 minutes. The pH of the wastewater was then adjusted to 7.7 with 20% KOH. After the pH adjustment, it was re-filtered with 0.22 μm nylon filter unit system. In two six-well plates (351146 Falcon), six different conditions were set up.

One plate was dedicated for filter-sterilized winery wastewater and other plate was dedicated for autoclaved—filter sterilized wastewater.
1. Winery wastewater (WW) only
2. Regular cell medium+2% glucose
3. Winery wastewater+NaNO$_3$ (same concentrations as in #2)
4. Winery wastewater+other components in cell medium (same concentrations as in #2)
5. 50% winery wastewater (50% of wastewater+50% regular cell medium)
6. 25% winery wastewater (25% of wastewater+75% regular cell medium)

The final volume for each well was 6 ml. Initial cell concentration for each well was 0.5 mg/ml. Intensity of light was set at 3-5 µmol/m$^2$s$^{-1}$ photons. The speed of the orbital shaker was set at 140 rpm. The experiment was carried out at room temperature for two weeks. At the end of the experimental period 1 ml of cell culture from each condition was transferred to pre-measured Eppendorf tubes, and spun down to obtain cell pellets. The cell pellets were freeze dried and the final dried cell weight was determined by subtracting the final weight of each Eppendorf tube containing the dried cells to the initial Eppendorf tube weight.

Results

Figure 6:
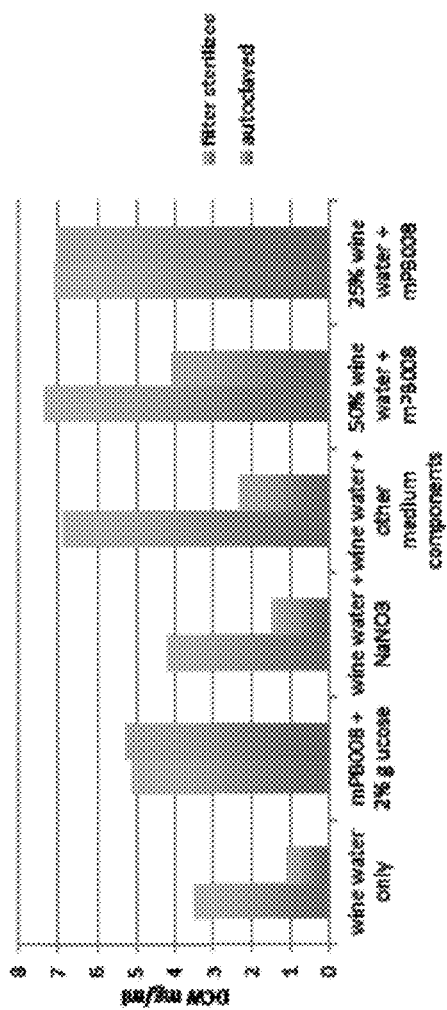
FIG. 6 shows the DCW of UTEX 1185 grown under different winery wastewater conditions. For each condition, the bar on the left represents filter sterilized and the bar on the right represents autoclaved.
Figure 6:
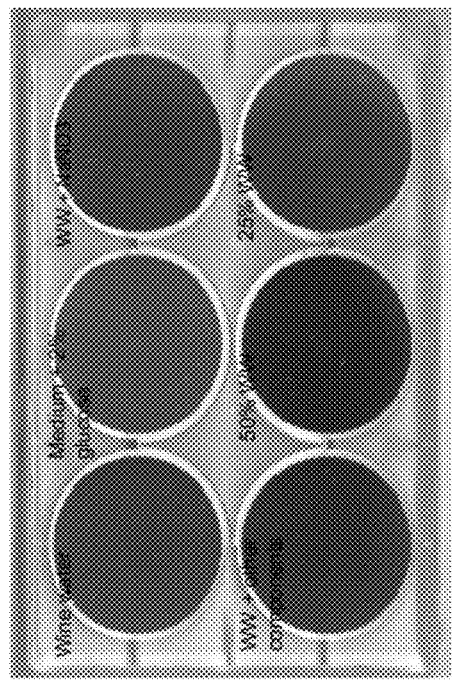
Figure 6:
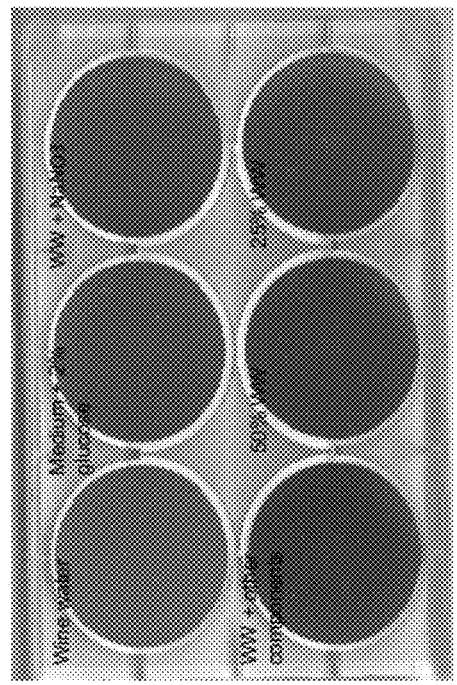

As shown in FIG. 6, use of winery wastewater resulted in growth of UTEX 1185 as measured by dry cell weight (DCW).

Example 5

Microalgae and Culture Condition

*Botryococcus sudeticus* UTEX 2629 was obtained from the culture collection of algae at the University of Texas (Austin, Tex. USA). Initial culture was grown in an Erlenmeyer 250 ml flask containing 120 ml modified BG11 medium with 2% glucose at 25° C. room temperature with aluminum foil loosely covering the flask on an orbital shaker at 130 rpm under alternating two 40 W natural sunshine (392316, Philips) and two 40 W plant and aquarium (392282, Philips) fluorescent light bulbs. The culture medium contained the following components per 1 L of deionized water: 17.6 mM NaNO$_3$, 0.43 mM K$_2$HPO$_4$, 0.3 mM MgSO$_4$ 7H$_2$O, 0.2 mM CaCl$_2$ 2H$_2$O, 0.03 mM Citric acid H$_2$O, 0.02 mM Ammonium Ferric Citrate, 0.002 mM Na$_2$EDTA 2H$_2$O, 0.18 mM Na$_2$CO$_3$, 1 ml of BG11 metal solution (2.86 g H$_3$BO$_3$, 1.81 g MnCl$_2$ 4H$_2$O, 0.22 g ZnSO$_4$ 7H$_2$O, 0.39 g Na$_2$MoO$_4$ 2H$_2$O, 0.079 g CuSO$_4$5H$_2$O, 49.4 mg Co(NO$_3$)$_2$ 6H$_2$O in 1 L dI water), 10 mM HEPES, 1 ml of each of three vitamins (0.1 mM B12, 0.1 mM Biotin, 6.5 mM Thiamine dissolved separately in 50 mM HEPES pH7.8. Each of the vitamin solutions were filter sterilized before use). Final pH of the medium was adjusted to 7.8 with 20% KOH before autoclaving the medium. The vitamin solutions were added after autoclaving the medium.

Once the initial culture reached a certain confluence, its concentration was measured by drying 5 ml of cell culture at 125° C. using a moisture analyzer (HG63 Mettler Toledo).

Experimental Procedure

Two liters of winery wastewater was obtained from Scheid Vineyards in Salinas, Calif. The wastewater was derived from: water used to wash grapes prior to processing, crushing, washing, tank disinfection, and filtering. After a washing step, the wastewater generally contained about 2-4% glucose. The specific sample of wastewater used for this experiment contained 1.7% to 1.9% glucose. One liter of wastewater was filtered with a 0.22 µm filter system unit to sterilize it and pH was adjusted to 7.5 with 20% KOH. Another one liter was autoclaved to sterilize it at 121° C. for 40 minutes. The pH of the wastewater was then adjusted to 7.7 with 20% KOH. After the pH adjustment, it was re-filtered with 0.22 µm nylon filter unit system. In two six-well plates (351146 Falcon), six different conditions were set up. One plate was dedicated for filter-sterilized winery wastewater and other plate was dedicated for autoclaved—filter sterilized wastewater.
1. Winery wastewater (WW) only
2. Regular cell medium+2% glucose
3. Winery wastewater+NaNO$_3$ (same concentrations as in #2)
4. Winery wastewater+other components in cell medium (same concentrations as in #2)
5. 50% winery wastewater (50% of wastewater+50% regular cell medium)
6. 25% winery wastewater (25% of wastewater+75% regular cell medium)

The final volume for each well was 6 ml. Initial cell concentration for each well was 0.5 mg/ml. Intensity of light was set at 3-5 µmol/m$^2$s$^{-1}$ photons. The speed of the orbital shaker was set at 140 rpm. The experiment was carried out at room temperature for two weeks. At the end of the experimental period 1 ml of cell culture from each condition was transferred to pre-measured Eppendorf tubes, and spun down to obtain cell pellets. The cell pellets were freeze dried and the final dried cell weight was determined by subtracting the final weight of each Eppendorf tube containing the dried cells to the initial Eppendorf tube weight.

Results

Figure 7:
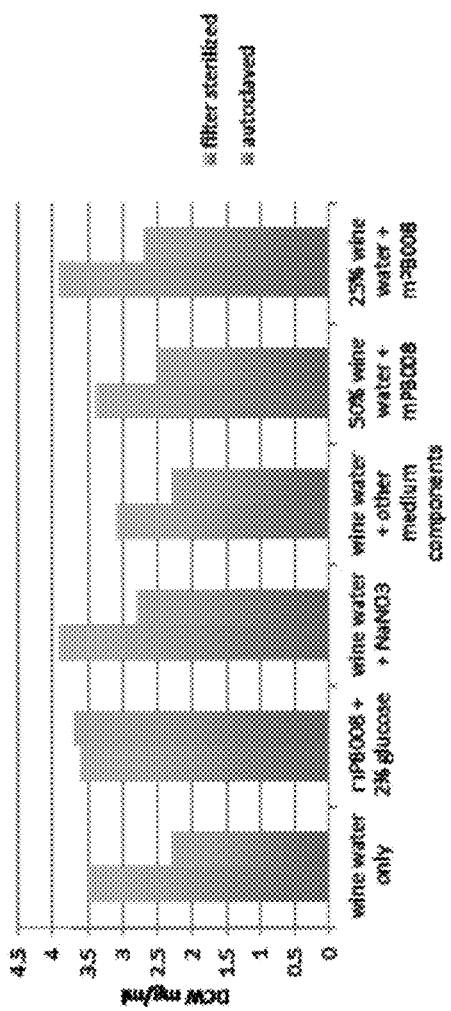
FIG. 7 shows the DCW of UTEX 2629 grown under different winery wastewater conditions. For each condition, the bar on the left represents filter sterilized and the bar on the right represents autoclaved.
Figure 7:
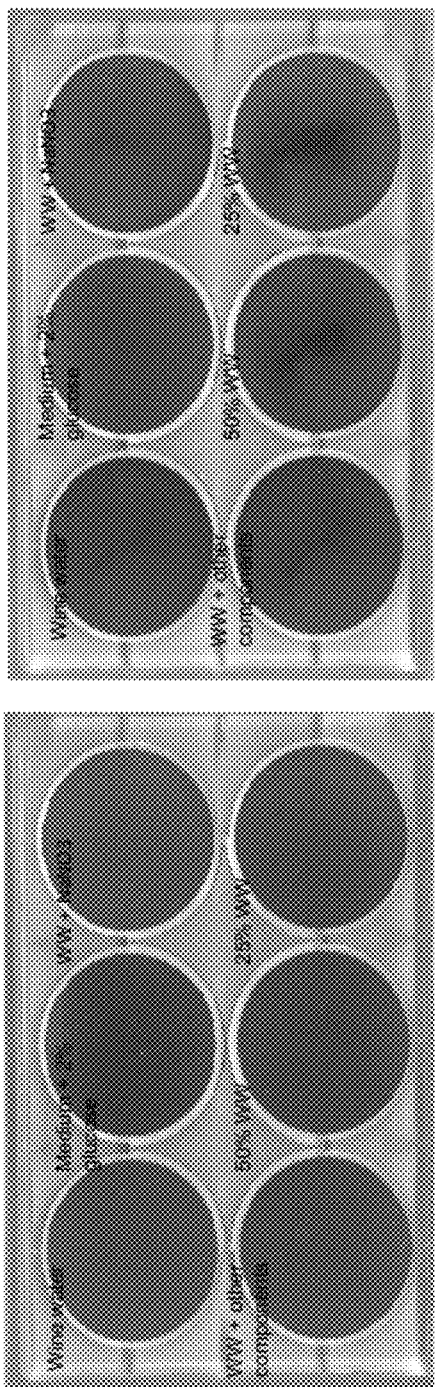

As shown in FIG. 7, use of winery wastewater resulted in growth of UTEX 2629 as measured by dry cell weight (DCW).

Example 6

Microalgae and Culture Condition

*Botryococcus braunii* race A strains UTEX 572 and UTEX 2441 were obtained from the algae culture collection at the University of Texas (Austin, Tex. USA). Initial cultures were grown separately in Erlenmeyer 250 ml flasks containing 120 ml modified BG11 medium with 2% glucose at 25° C. with aluminum foil loosely covering the flasks on an orbital shaker at 130 rpm under fluorescent lighting composed of two different bulbs (40 W natural sunshine and 40 W plant and aquarium fluorescent light bulbs). Modified BG11 medium contains following components per 1 L of deionized water: 17.6 mM NaNO3, 0.22 mM K2HPO4, 0.3 mM MgSO4 7H$_2$O, 0.2 mM CaCl2 2H2O, 0.03 mM Citric acid H2O, 0.046 mM Ammonium Ferric Citrate, 0.002 mM Na2EDTA 2H2O, 0.18 mM Na2CO3, 1 ml of BG11 metal solution (2.86 g H3BO3, 1.81 g MnCl2 4H2O, 0.22 g ZnSO4 7H$_2$O, 0.39 g Na2MoO4 2H2O, 0.079 g CuSO4 5H2O, 49.4 mg Co(NO3)2 6H2O in 1 L deionized water), 10 mM HEPES, 0.5 g Casein Hydrolysate, and 1 ml of each of three vitamins (0.1 mM B12, 0.1 mM Biotin, 6.5 mM Thiamine dissolved separately in 50 mM HEPES pH7.8. Each of the vitamin solutions were filter sterilized before use). The final pH of the medium was adjusted to 7.8 with 20% KOH before autoclaving the medium. The vitamin solutions were added after autoclaving the medium. Once the initial culture reached a certain confluence, its concentration was measured by drying 5 ml of cell culture at 125° C. using a moisture analyzer (HG63 Mettler Toledo).

Experimental Procedure and Growth Measurement

Two liters of winery wastewater was obtained from Scheid Vineyards in Salinas, Calif. The wastewater was derived from: water used to wash grapes prior to processing, crushing, washing, tank disinfection, and filtering. After a washing step, the wastewater usually contained about 2-4% glucose. The specific sample of wastewater used for this experiment contained 1.7% to 1.9% glucose. One liter of wastewater was filtered with a 0.22 µm filter system unit to sterilize it and pH was adjusted to 7.5 with 20% KOH. Another one liter was autoclaved to sterilize it at 121° C. for 40 minutes. The pH of the wastewater was then adjusted to 7.7 with 20% KOH. Then it was re-filtered with 0.22 µm nylon filter unit system. In two six-well plates (351146 Falcon), six different conditions were set up. One plate was dedicated for filter-sterilized winery wastewater and other plate was dedicated for autoclaved—filter sterilized wastewater.

1. Winery wastewater (WW) only
2. Regular cell medium+2% glucose
3. Winery wastewater+NaNO$_3$ (same concentrations as in #2)
4. Winery wastewater+other components in cell medium (same concentrations as in #2)
5. 50% winery wastewater (50% of wastewater+50% regular cell medium)
6. 25% winery wastewater (25% of wastewater+75% regular cell medium)

The final volume for each well was 6 ml. Initial cell concentration for each well was 1 mg/ml. Intensity of light was set at 3-5 µmol/m$^2$s$^{-1}$ photons. The speed of the orbital shaker was set at 140 rpm. The experiment was carried out at room temperature for two weeks. At the end of the experimental period 1 ml of cell culture from each condition was transferred to pre-measured Eppendorf tubes, and spun down to obtain cell pellets. The cell pellets were freeze dried and the final dried cell weight was determined by subtracting the final weight of each Eppendorf tube containing the dried cells to the initial Eppendorf tube weight.

Results

Figure 8:
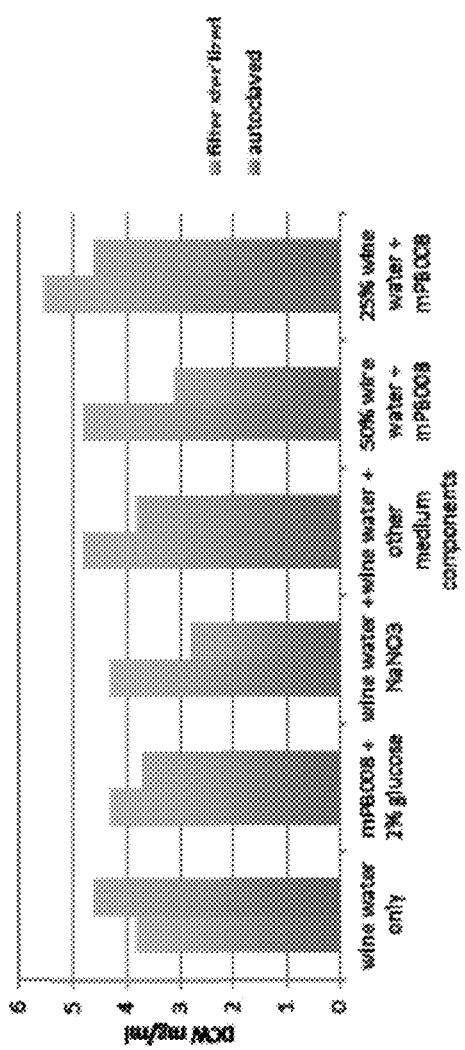
FIG. 8 shows the DCW of UTEX 572 grown under different winery wastewater conditions. For each condition, the bar on the left represents filter sterilized and the bar on the right represents autoclaved.
Figure 8:
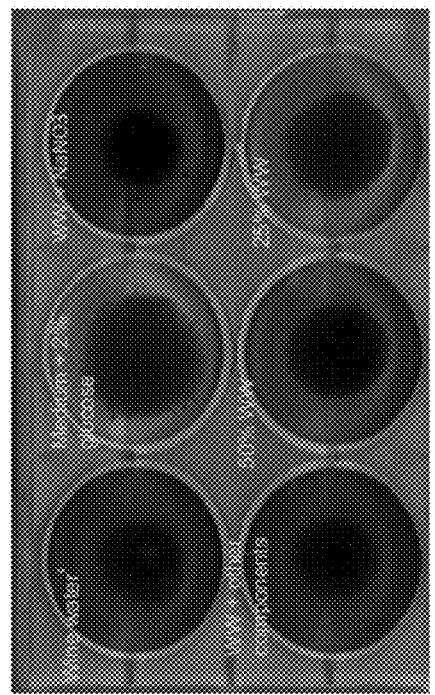
Figure 8:
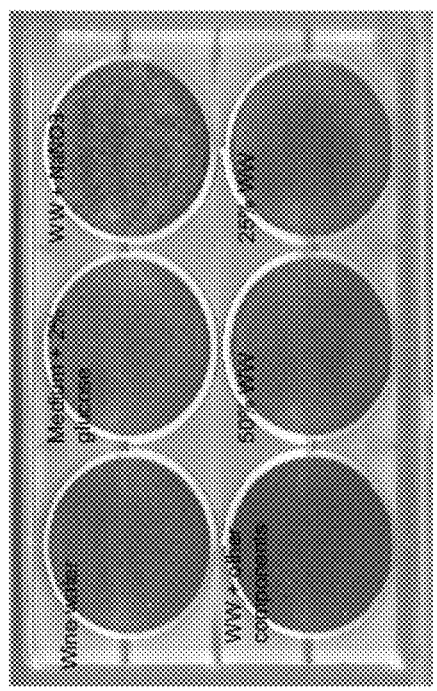
Figure 9:
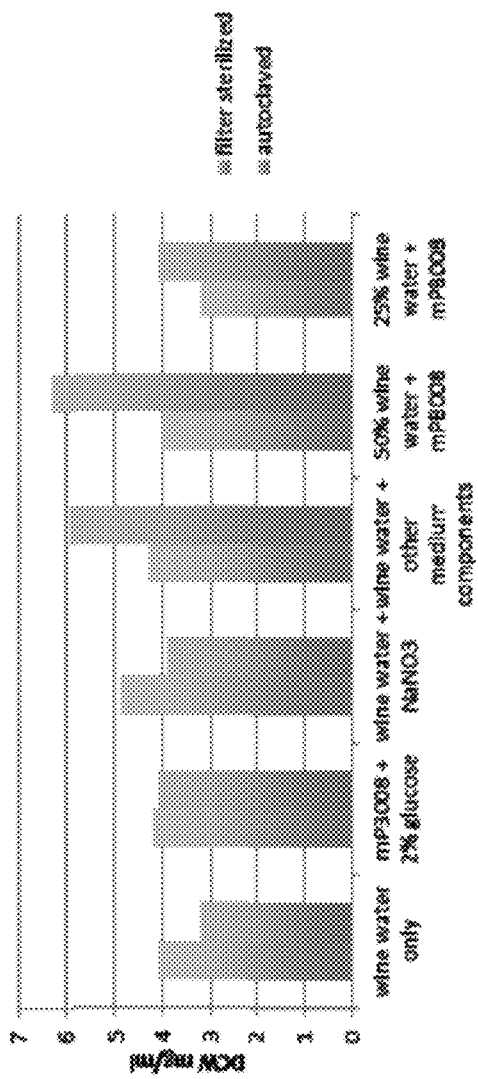
FIG. 9 shows the DCW of UTEX 2441 grown under different winery wastewater conditions. For each condition, the bar on the left represents filter sterilized and the bar on the right represents autoclaved.
Figure 9:
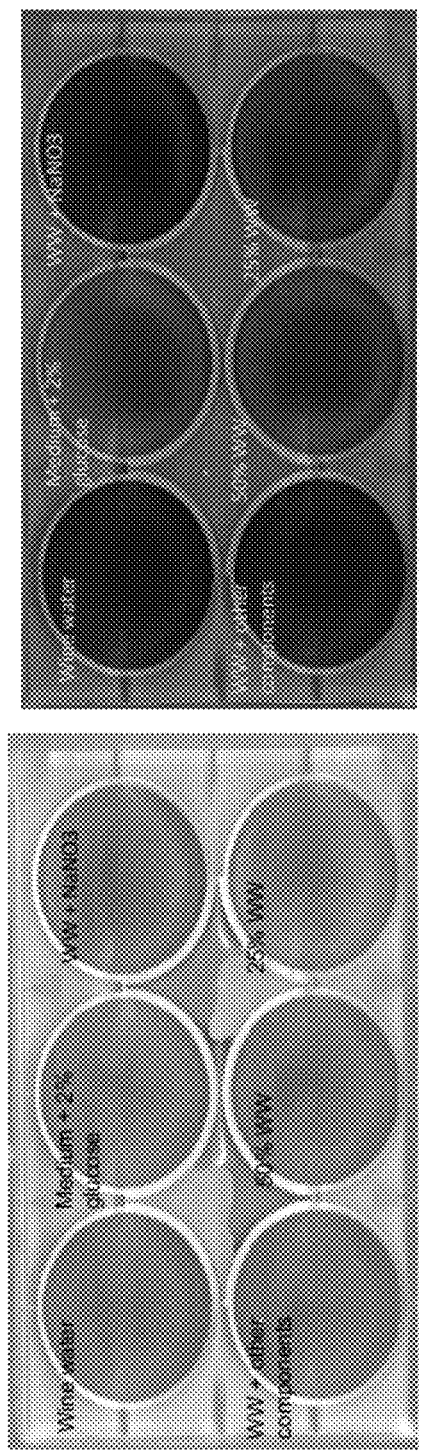

As shown in FIG. 8, use of winery wastewater resulted in growth of UTEX 572 as measured by dry cell weight (DCW). As shown in FIG. 9, use of winery wastewater resulted in growth of UTEX 2441 as measured by dry cell weight (DCW).

Example 7

Cultivation of Microalgae with Fruit Derived Wastewater

Materials and Methods

Strains and Media

Microalgae strains (e.g., *Chlamydomonas, Botryococcus, Neochloris, Thraustochytrium, Chlorella, Monodus, Nannochloropsis, Crypthecoides, Haematococcus, Nitzschia, Navicula*, Cyanophyta, Chlorophyta, Rhodophyta, Cryptophyta, Chlorarachniophyta, Haptophyta, Euglenophyta, Heterokontophyta, Diatoms and/or those described in the description above) are obtained from, e.g., the algae culture collection at the University of Texas (Austin, Tex. USA). Stock culture is grown, e.g., in Erlenmeyer 250 ml flasks containing the appropriate medium (see, e.g., manufacturer's instructions) at about 25° C. room temperature with dim light (e.g., 4-5 µmol/m$^2$s$^{-1}$ photons) on an orbital shaker at about 130 rpm. An appropriate carbon source is used in the culture media, e.g., glucose. Dim lighting can be composed of two different bulbs, e.g., 40 W natural sunshine (392316 Philips) and 40 W plant and aquarium fluorescent light bulbs (392282 Philips). The final pH of the medium is adjusted as appropriate for the particular strain. See, e.g., manufacturer's instructions.

Experimental Procedure and Growth Measurement

Two liters of wastewater is obtained. The wastewater is derived from water used to wash fresh or dried fruit prior to packaging, or from processes used in the fruit industry, or from water used in the processing of grapes at a winery. The wastewater typically contains 2-4% glucose. The wastewater is filtered, e.g., with a 0.22 um filter system unit to sterilize it and pH is generally adjusted to about neutral (pH 7.0). In one six-well plate (351146 Falcon), six different conditions are set up.

1. Wastewater (RW) only
2. Regular cell medium+2% glucose
3. Wastewater+NaNO3 (same concentrations as in #2)
4. Wastewater+other components in cell medium (same concentrations as in #2)
5. 50% wastewater (50% of wastewater+50% regular cell medium)
6. 25% wastewater (25% of wastewater+75% regular cell medium)

The final volume for each well is 6 ml. Initial cell concentration for each well is O.D. 0.3 at 750 nm. Intensity of light is set at 3-5 µmol/m$^2$s$^{-1}$ photons. The speed of the orbital shaker is set at 140 rpm. The experiment is carried out at room temperature for 4 days. At the end of the experimental period 1 ml of cell culture from each condition is transferred to pre measured eppendorf tubes, and they are spun down to obtain cell pellets. The cell pellets are freeze dried and the final dried cell weight is determined by subtracting final weight of the eppendorf tube containing dried cells from the initial eppendorf tube weight.

Measurement of Material of Interest

The amount of material of interest (hydrocarbon, lipid, etc.) in the media is measured using standard means known in the art, e.g., GC-MS or Nile Red as described above. For example, in 1 ml of algal suspension, 4 ul of Nile Red solution in acetone (250 ug/ml) is added. The mixture is vortexed during incubation at room temperature. After incubation, 100-200 ul of stained algal samples are transferred into individual wells in a 96-well plate. Fluorescence is measured on, e.g., a Molecular Devices 96 well plate spectrofluorometer with a 490 nm excitation and 585 nm emission wavelength with 530 emission filter cut off. In order to determine the relative fluorescence intensity of algal samples, blank (Nile Red alone in the medium) is subtracted from the fluorescence intensity.

Results

Use of fruit wastewater results in growth of microalgae as measured by dry cell weight (DCW). Material of interest (e.g., hydrocarbon or lipid) is produced by the experimental microalgae strain.

While the invention has been particularly shown and described with reference to a preferred aspect and various alternate aspects, it will be understood by persons skilled in the relevant art that various changes in form and details can be made therein without departing from the spirit and scope of the invention.

All references, issued patents and patent applications cited within the body of the instant specification are hereby incorporated by reference in their entirety, for all purposes.

The invention claimed is:

1. A method for cultivating a microalgae capable of heterotrophic growth by providing a light signal to initiate a light-activated metabolism, comprising:
   incubating the microalgae under a heterotrophic growth condition for a period of time sufficient to allow the microalgae to grow, wherein the heterotrophic growth condition comprises a media comprising a fruit wastewater, and wherein the heterotrophic growth condition further comprises light having a wavelength between 360 and 700 nm, required to initiate the light-activated metabolism, and the intensity of the light is less than 0.8 µmol photons/m$^2$s,
   wherein the light-activated metabolism includes a life cycle, a circadian rhythm, cell division, a biosynthetic pathway, or a transport system,
   wherein the microalgae is a *Botryococcus sudeticus* (UTEX 2629) strain or a *Neochloris oleabundans* (UTEX 1185) strain,
   wherein the irradiation of the light is applied in a cyclic pattern of light and dark at a ratio between 6 hours (light): 18 hours (dark) or 23 hours (light): 1 hours (dark).

2. The method of claim 1, wherein the fruit wastewater is raisin wastewater or wine wastewater, and wherein the light irradiance is between 0.1 to less than 0.8 µmol photons/m$^2$s.

3. The method of claim 1, wherein the fruit wastewater is raisin wastewater or wastewater from a winery.

4. The method of claim 1, wherein the intensity of the light is between 0.01 and less than 0.8 µmol photons/m$^2$s.

5. The method of claim 1, further comprising producing a material from the microalgae.

6. The method of claim 5, wherein the material is a polysaccharide, a lipid, or a hydrocarbon.

7. The method of claim 5, further comprising processing the material.

8. The method of claim 7, wherein the processing of the material produces a processed material.

9. The method of claim 8, wherein the processed material is selected from the group consisting of a biodiesel, jet fuel, a cosmetic, a pharmaceutical agent, a surfactant, and a renewable diesel.

10. The method of claim 1, wherein the growth rate of the microalgae is higher than a second microalgae incubated under a second heterotrophic growth condition for a period of time sufficient to allow the microalgae to grow, wherein the second heterotrophic growth condition comprises a growth media comprising a non-wastewater carbon source.

11. A culture for cultivating a microalgae capable of heterotrophic growth, wherein the culture comprises the microalgae placed under a heterotrophic growth condition for a period of time sufficient to allow the microalgae to grow, wherein the heterotrophic growth condition comprises a media comprising a fruit wastewater, and wherein the heterotrophic growth condition further comprises light having a wavelength between 360 and 700 nm, required to initiate a light-activated metabolism, and the intensity of the light is less than 0.8 µmol photons/m$^2$s,
   wherein the light-activated metabolism includes a life cycle, a circadian rhythm, cell division, a biosynthetic pathway, or a transport system,
   wherein the microalgae is a *Botryococcus sudeticus* (UTEX 2629) strain, or a *Neochloris oleabundans* (UTEX 1185) strain,
   wherein the irradiation of the light is applied in a cyclic pattern of light and dark at a ratio between 6 hours (light): 18 hours (dark) or 23 hours (light): 1 hours (dark).

12. The culture of claim 11, wherein the fruit wastewater is raisin wastewater or wine wastewater, and wherein the light irradiance is between 0.1 to less than 0.8 µmol photons/m$^2$s.

13. The culture of claim 11, wherein the fruit wastewater is raisin wastewater or wastewater from a winery.

14. The culture of claim 11, wherein the intensity of the light is between 0.01 and less than 0.8 µmol photons/m$^2$s.

15. The culture of claim 11, wherein the fruit wastewater is the only carbon source in the media.

16. The culture of claim 11, wherein the fruit wastewater is the only source of glucose in the media or the fruit wastewater is the only source of sugar in the media.

* * * * *